(12) United States Patent
Downey et al.

(10) Patent No.: US 10,449,570 B2
(45) Date of Patent: Oct. 22, 2019

(54) SYSTEM AND METHOD FOR DRIVING AN ULTRASONIC HANDPIECE WITH A LINEAR AMPLIFIER

(71) Applicant: Stryker Corporation, Kalamazoo, MI (US)

(72) Inventors: Adam D. Downey, Kalamazoo, MI (US); Neal R. Butler, Acton, MA (US); Scott A. Rhodes, North Andover, MA (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 15/805,849

(22) Filed: Nov. 7, 2017

(65) Prior Publication Data
US 2018/0056328 A1     Mar. 1, 2018

Related U.S. Application Data

(63) Continuation of application No. PCT/US2016/031651, filed on May 10, 2016.
(Continued)

(51) Int. Cl.
*A61B 18/14* (2006.01)
*B06B 1/02* (2006.01)
(Continued)

(52) U.S. Cl.
CPC .... *B06B 1/0253* (2013.01); *A61B 17/320068* (2013.01); *A61F 9/00745* (2013.01); *B06B 1/0246* (2013.01); *H03F 1/0216* (2013.01); *A61B 17/142* (2016.11); *A61B 18/14* (2013.01); *A61B 90/98* (2016.02);
(Continued)

(58) Field of Classification Search
CPC . A61F 9/00745; B06B 1/0246; B06B 1/0253; B06B 2201/55; B06B 2201/76; H03F 2200/541; H03F 3/45475
See application file for complete search history.

(56) References Cited

U.S. PATENT DOCUMENTS 3,746,897 A    7/1973  Karatjas
3,889,166 A    6/1975  Scurlock
(Continued)

FOREIGN PATENT DOCUMENTS

CN    101999205 A    3/2011
CN    103327139 A    9/2013
(Continued)

OTHER PUBLICATIONS

International Search Report for Application No. PCT/US2016/031651 dated Oct. 10, 2016, 7 pages.
(Continued)

*Primary Examiner* — Muhammad S Islam
(74) *Attorney, Agent, or Firm* — Howard & Howard Attorneys PLLC

(57) ABSTRACT

A control console for a powered surgical tool. The console includes a transformer that supplies the drive signal to the surgical tool. A linear amplifier with active resistors selectively ties the ends of the transformer primary winding between ground and the open circuit state. Feedback voltages from the transformer windings regulate the resistances of the active resistors.

24 Claims, 22 Drawing Sheets

Related U.S. Application Data

(60) Provisional application No. 62/159,672, filed on May 11, 2015.

(51) Int. Cl.

| | | |
|---|---|---|
| *A61B 17/32* | (2006.01) | |
| *A61F 9/007* | (2006.01) | |
| *H03F 1/02* | (2006.01) | |
| *A61B 17/00* | (2006.01) | |
| *A61B 90/98* | (2016.01) | |
| *A61B 17/14* | (2006.01) | |
| *A61B 18/00* | (2006.01) | |
| *A61B 18/18* | (2006.01) | |
| *H02M 3/158* | (2006.01) | |
| *H03F 3/45* | (2006.01) | |

(52) U.S. Cl.
CPC ............ *A61B 2017/0003* (2013.01); *A61B 2017/00017* (2013.01); *A61B 2017/00199* (2013.01); *A61B 2017/00477* (2013.01); *A61B 2017/00973* (2013.01); *A61B 2018/00029* (2013.01); *A61B 2018/00577* (2013.01); *A61B 2018/1807* (2013.01); *A61B 2217/005* (2013.01); *A61B 2217/007* (2013.01); *B06B 2201/55* (2013.01); *B06B 2201/76* (2013.01); *H02M 3/158* (2013.01); *H03F 3/45475* (2013.01); *H03F 2200/541* (2013.01)

(56) References Cited

U.S. PATENT DOCUMENTS

| | | | |
|---|---|---|---|
| 3,975,650 A | 8/1976 | Payne | |
| 4,271,371 A * | 6/1981 | Furuichi | B06B 1/0253 310/316.01 |
| 4,336,509 A | 6/1982 | Bernitz | |
| 4,453,073 A | 6/1984 | Bredenkamp | |
| 4,554,477 A | 11/1985 | Ratcliff | |
| 4,642,581 A | 2/1987 | Erickson | |
| 5,136,199 A * | 8/1992 | Kawai | B06B 1/0253 310/316.01 |
| 5,394,047 A * | 2/1995 | Scharlack | G01N 1/286 310/316.01 |
| 5,930,121 A | 7/1999 | Henry | |
| 6,819,027 B2 | 11/2004 | Saraf | |
| 7,794,414 B2 | 9/2010 | Rabiner et al. | |
| 7,857,783 B2 | 12/2010 | Kadziauskas et al. | |
| 8,000,112 B2 | 8/2011 | Zhang | |
| 8,115,366 B2 | 2/2012 | Hoffman et al. | |
| 8,197,502 B2 | 6/2012 | Smith et al. | |
| 8,236,020 B2 | 8/2012 | Smith et al. | |
| 9,060,775 B2 | 6/2015 | Wiener et al. | |
| 9,072,539 B2 | 7/2015 | Messerly et al. | |
| 10,022,567 B2 | 7/2018 | Messerly et al. | |
| 10,022,568 B2 | 7/2018 | Messerly et al. | |
| 2007/0247877 A1 * | 10/2007 | Kwon | H02M 3/3372 363/25 |
| 2007/0249941 A1 | 10/2007 | Salehi et al. | |
| 2010/0102672 A1 | 4/2010 | Hoffman et al. | |
| 2010/0125292 A1 | 5/2010 | Wiener et al. | |
| 2011/0241576 A1 | 10/2011 | Paschke | |
| 2012/0078139 A1 | 3/2012 | Aldridge et al. | |
| 2012/0221031 A1 | 8/2012 | Smith et al. | |
| 2013/0035679 A1 | 2/2013 | Orszulak | |
| 2014/0049299 A1 * | 2/2014 | Chu | G10K 11/346 327/129 |
| 2015/0098307 A1 * | 4/2015 | Lei | B06B 1/0215 367/137 |
| 2017/0071621 A1 | 3/2017 | Downey et al. | |

FOREIGN PATENT DOCUMENTS

| | | |
|---|---|---|
| GB | 2090705 A | 7/1982 |
| JP | 58-53195 A | 3/1983 |
| JP | S5853195 A | 3/1983 |
| WO | 2015021216 A1 | 2/2015 |

OTHER PUBLICATIONS

Machine-assisted English translation for JPS 58-53195 extracted from PAJ database on Dec. 6, 2017, 3 pages.

Gentile, Ken, "Driving a Center-Tapped Transformer with a Balanced Current-Output DAC", Analog Devices, AN-912, Application Note, 2007, pp. 1-12.

Svilanis, G., et al., "Power Amplifier for Ultrasonic Transducer Excitation", ISSN 1392-2114, ULTRAGARSAS, Nr. 1 (58), 2006, pp. 30-36.

EPO, "ISA Search Report and Written Opinion for PCT/US2016/031651".

English language abstract for CN 101999205 extracted from espacenet.com database on Jun. 3, 2019, 1 page.

English language abstract and machine-assisted English translation for CN 103327139 extracted from espacenet.com database on Jun. 3, 2019, 20 pages.

\* cited by examiner

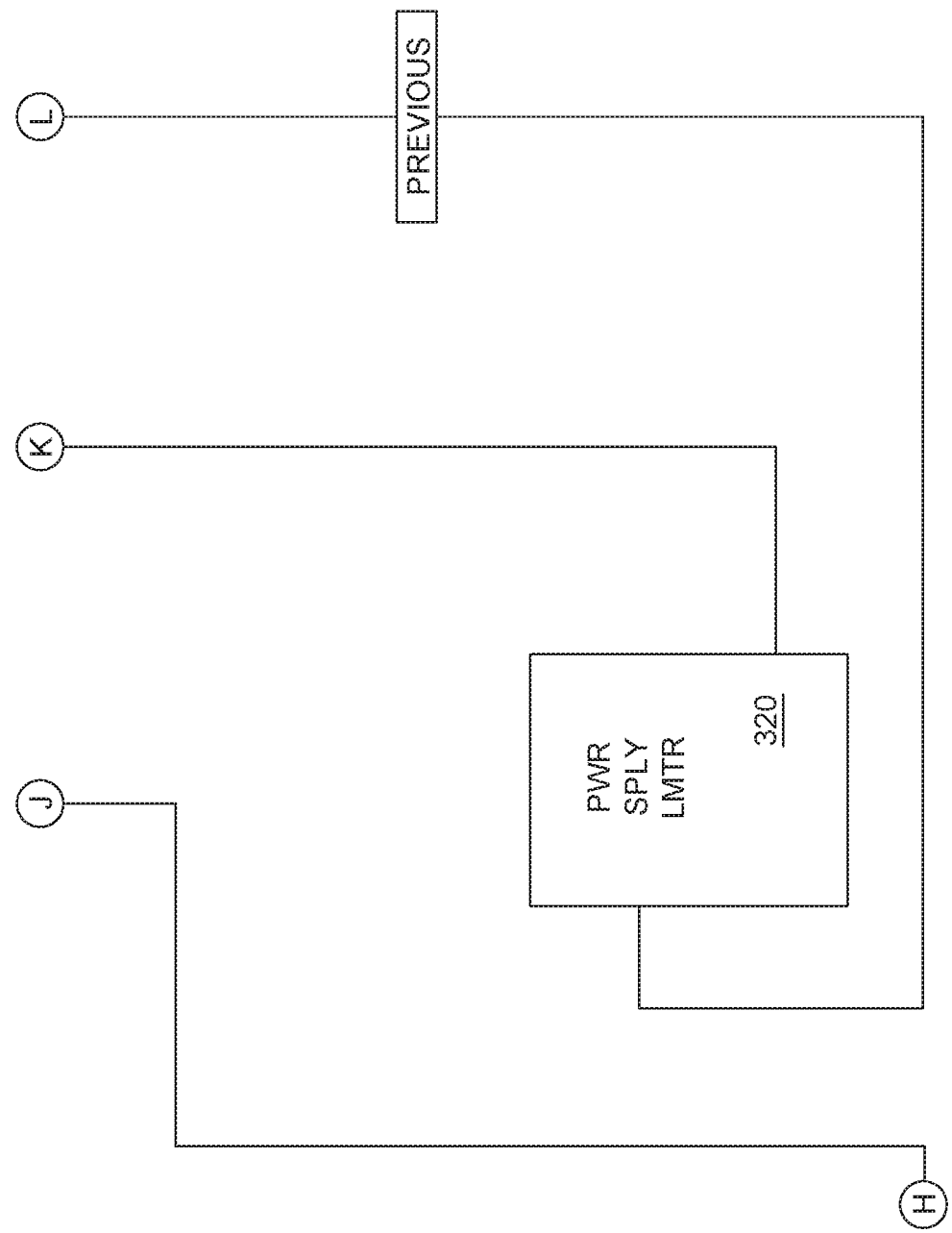

SYSTEM AND METHOD FOR DRIVING AN ULTRASONIC HANDPIECE WITH A LINEAR AMPLIFIER

FIELD OF THE INVENTION

This invention relates generally to an ultrasonically driven surgical tool system. More particularly, this invention relates to an ultrasonic tool system with a console capable of outputting drive signals over a wide range of frequencies and a wide range of voltages.

BACKGROUND OF THE INVENTION

Ultrasonic surgical instruments are useful surgical instruments for performing certain medical and surgical procedures. Generally, an ultrasonic surgical tool includes a handpiece that contains at least one piezoelectric driver. A tip is mechanically coupled to the driver and extends forward from the housing or shell in which the driver is disposed. The tip has a head. The head is provided with features, often teeth or flutes, dimensioned to accomplish a specific medical/surgical task. The handpiece is part of an ultrasonic tool system. The system also includes a control console. The control console supplies an AC drive signal to the driver. Upon the application of the drive signal to the driver, the driver cyclically expands and contracts. The expansion/contraction of the driver induces a like movement in the tip and, more particularly, the head of the tip. When the tip so moves, the tip is considered to be vibrating. The vibrating head of the tip is applied against tissue to perform a specific surgical or medical task. For example, some tip heads are applied against hard tissue. One form of hard tissue is bone. When this type of tip head is vibrated, the back and forth vibrations of the tip head remove, saw, the adjacent hard tissue. Other tip heads are designed to be placed against soft tissue. When this tip head vibrates the teeth often remove the tissue by a cutting action. Other ultrasonic tips remove tissue by inducing cavitation in the tissue and surrounding fluid. Cavitation occurs as a result of the tip head moving back and forth. Specifically, as a result of these vibrations, small cavities form in the fluid located immediately adjacent the tissue. These cavities are very small zones of extremely low pressure. A pressure differential develops between contents of the cells forming the tissue and these cavities. Owing to the magnitude of this pressure differential, the cell walls burst. The bursting of these cell walls, removes, ablates, the cells forming the tissue.

The head of an ultrasonic tip is often relatively small. Some heads have diameters of less than 1.0 cm. An ultrasonic tool essentially only removes the tissue adjacent to where the head is applied. Owing to the relative small surface area of their heads, ultrasonic handpieces have proven to be useful tools for precisely removing both hard and soft tissue.

Some ultrasonic tips are provided with a through bore. Simultaneously with the application of a drive signal to this type of tip, a suction is drawn through the bore. The suction draws away the debris created by tissue removal process. This is why some ultrasonic tools are sometimes called ultrasonic aspirators.

For an ultrasonic surgical instrument, sometimes called a handpiece or a tool, to efficiently function, a drive signal having the appropriate characteristics should be applied to the tool. If the drive signal does not have the appropriate characteristics, the tip head may undergo vibrations of less than optimal amplitude. If the handpiece is in this state, the ability of the handpiece to, at a given instant, remove tissue may be appreciably reduced.

One means of ensuring that an ultrasonic handpiece operates efficiently is to apply a drive signal to the handpiece that is at the resonant frequency of the handpiece. When the drive signal is at a given voltage or current, the application of the drive signal at the resonant frequency induces vibrations in the tip that are large in amplitude in comparison to the application of the same voltage at a frequency that is off resonance.

Still other ultrasonic tool systems are designed to apply a drive signal at the anti-resonant frequency of the handpiece. The anti-resonant frequency may be a frequency at which the handpiece would have the highest impedance. Sometimes it is desirable to apply a drive signal that is at a frequency somewhere between the resonant and anti-resonant frequencies of the handpiece.

Further, the amplitude of the tip vibrations is also related to the potential, the voltage, of the drive signal. Generally, the amplitude of the tip vibrations is proportional to the voltage of the drive signal. There is however, typically a voltage that, once exceeded, will not result in an increase in the amplitude of the tip vibrations.

Internal to the console are the components that generate the drive signal. Generally, the components integral with the console can be broken down into four main sub-assemblies. A first sub-assembly includes the sensing components. These components monitor the characteristics of the drive signal sourced to the handpiece. An input/output assembly serves as an interface through which the surgeon enters commands regarding the characteristics of the drive signal that is to be applied to the handpiece and over which information regarding the status of the operation of the system is displayed. The third assembly is the controller. The controller, based on the user-entered commands and the signals from the sensing components, generates control signals. The controller also generates information that is presented on the input/output assembly.

The control signals generated by the controller are applied to the fourth sub-assembly of console components, the amplifier. This is because, owing to the limitations of components forming the controller, the control signals typically have potentials of 10 Volts or less and often 5 Volts or less. For the drive signal to induce the desired contractions and expansions of the transducers, the signal typically needs to have a potential of at least 500 volts and often 1000 volts. The amplifiers of many consoles amplify the control signal so the output signal produced by the amplifier is at the potential at which the output signal can function as the drive signal applied to the handpiece.

Applicant's SONOPET® Ultrasonic Aspirator includes a console with components designed to generate and apply a variable drive signal to the attached handpiece. Internal to the console is a resonance circuit. At the time of manufacture of the console, the inductance and capacitance of this resonance circuit are set as a function of the impedance of the specific handpiece with which the console is intended to be used. The characteristics of the drive signal output by the console are set as a function of the voltage across this impedance circuit.

The control consoles provided with many ultrasonic tool systems include amplifiers capable of outputting drive signals that, over narrow frequency ranges, foster the desired handpiece driver expansions and contractions. For example, some control consoles output drive signals that have a frequency between 25.2 kHz and 25.6 kHz. This type of control console works well with a handpiece that includes drivers designed for actuation by drive signals that have a frequency within this range of frequencies. If a handpiece with drivers designed to receive drive signals over a different frequency range is attached to the console, the responsiveness of the handpiece to the out of range drive signals will be less than optimal.

As a consequence of this limitation, if a facility wants to use ultrasonic handpieces to which appreciably different drive signals are applied, it may be necessary to provide plural control consoles. Specifically, one console would be used to provide drive signals to handpieces to which drive signals having a first set of characteristics are applied. A second console is used to provide drive signals to the handpieces to which drive signals having a second set of characteristics are applied. Having to provide these plural consoles that differ only in the form of the drive signals they generate adds to the expense and administrative burden of operating the facility using this equipment.

Further, a console may not generate the optimal drive signals for some operating states even when the console is generating the signals within the intended frequency range of drive signals the console is designed to produce. This is because at one or both ends of the range of voltages of the drive signals the console is intended to produce, the amplifier internal to the console may not provide a linear response to input signals used to establish the voltage of the drive signals.

In addition, some tips are designed to, when actuated, vibrate with a motion that is combination of two distinct motions. For example, some tips are designed to engage in vibrational motion that is the sum of two components. The first component is the longitudinal vibration. This is the back and forth vibration along the longitudinal axis of the tip. The second component is the rotational or torsional vibration. This motion is a back and forth rotational motion around the longitudinal axis of the tip. Generally, a tip able to vibrate simultaneously in two modes is referred to as a tip able to engage in a bi-modal vibration. A tip designed to vibrate simultaneously in three or more modes is referred to as a tip able to engage in multi-modal vibration.

For a tip to engage in bi-modal or multi-modal vibrations, it is desirable to apply a drive signal to the tip that is a composite of the signals best suited to drive the tip in each of its vibratory modes. Often these signals are at different frequencies. A console that can only generate drive signals over a narrow range of frequencies is often for unsuitable for generating a drive signal that is composite of components that have frequencies that may differ by 1,000 Hz or more.

SUMMARY OF THE INVENTION

This invention is directed to a new and useful ultrasonic tool system. The system of this invention includes a console to which a handpiece is attached. The console supplies the drive signal that actuates the drivers internal to the handpiece. It is a further feature of this invention, that the console is able to source drive signals over both a wide range of frequencies and a wide range of potentials. The console of this invention can thus be used to provide drive signals to different handpieces that require drive signals with different characteristics.

A further feature of the system of this invention is that the console is designed to have a relatively low internal energy loss. More specifically, the console of this invention, while having a relatively low internal energy loss is able to, when necessary, rapidly ramp up the potential of the drive signal applied to the handpiece drivers. This minimizes the time lag between when a handpiece tip is applied to tissue to perform a procedure and when the tip vibrates over the distance desired by the practitioner using the tip.

The console of this system includes an amplifier assembly that typically consists of: a linear amplifier; a power supply; and a transformer. The power supply applies a DC signal to a center tap of the primary winding of the transformer. The linear amplifier selectively pulls the opposed ends of the transformer primary winding to ground or essentially an open circuit state. The sequenced connection of the ends of the transformer primary winding to ground or the open circuit causes an AC signal to develop across the windings. This causes induces an AC signal, to appear across the transformer secondary winding. The signal that appears across the transformer secondary winding is the drive signal applied to the handpiece drivers.

The linear amplifier includes transistors tied to the ends of the transformer primary windings. The amplifier controls the application of signals to the transistors. The transistors, in turn, selectively connect and disconnect the ends of the primary winding to ground. The transistors thus function as active resistors.

In preferred versions of the invention, the linear amplifier includes a negative feedback loop. This negative feedback loop controls the application of signals to the transistors.

In preferred versions of the invention at least some voltage is always present at the gate or base of each transistor. This ensures the rapid response of the transistor when it is necessary to turn on the transistor. Also, in some preferred versions of the invention the transistors attached to the transformer primary winding are MOSFETs.

In preferred versions of the invention the voltage of the signal the power supply applies to the center tap can be varied.

A processor, also part of the control console, sets the DC voltage level of the signal output by the power supply and applies an input signal to the linear amplifier. More particularly, the processor sets the DC voltage of the signal output by the power supply so that the minimum voltage present across the transistors is ideally at least at a headroom voltage. This is to ensure that the transistors are always in saturation. The processor also normally maintains the voltage across the transistors to level that typically does not appreciably exceed the headroom voltage. This is to minimize the loss of heat by the transistors. Also by maintaining a headroom voltage, the amplifier can rapidly increase the potential of the drive signal without having the initially increased drive signal appear as a clipped signal.

The processor regulates the signals output by the linear amplifier and the power supply to substantially eliminate the possibility that, when the voltage of the drive signal is increased, a jump in primary winding voltage will take the transistors out of saturation. The processor regulates the signals output by the power supply so that when the voltage of the drive signal is reduced, the center tap voltage is not allowed to drop so a subsequent need to increase the voltage the drive signal will not appreciably slow the increase in this voltage.

While one specific form of this invention is an ultrasonic surgical tool system it should be understood that the console of this invention may have other applications. Thus, the console of this tool system may be employed to apply an AC drive signal to powered surgical handpiece where the power generating unit is assembly other than a set of ultrasonic drivers.

BRIEF DESCRIPTION OF THE DRAWINGS

The invention is pointed out with particularity in the claims. The above and further features and advantages of this invention are understood from the following Detailed Description taken in conjunction with the accompanying drawings in which:

FIG. 15A-15D are assembled together to represent the software modules run on the processor internal to the control console to regulate the characteristics of the drive signal output by the console

DETAILED DESCRIPTION

Figure 1:
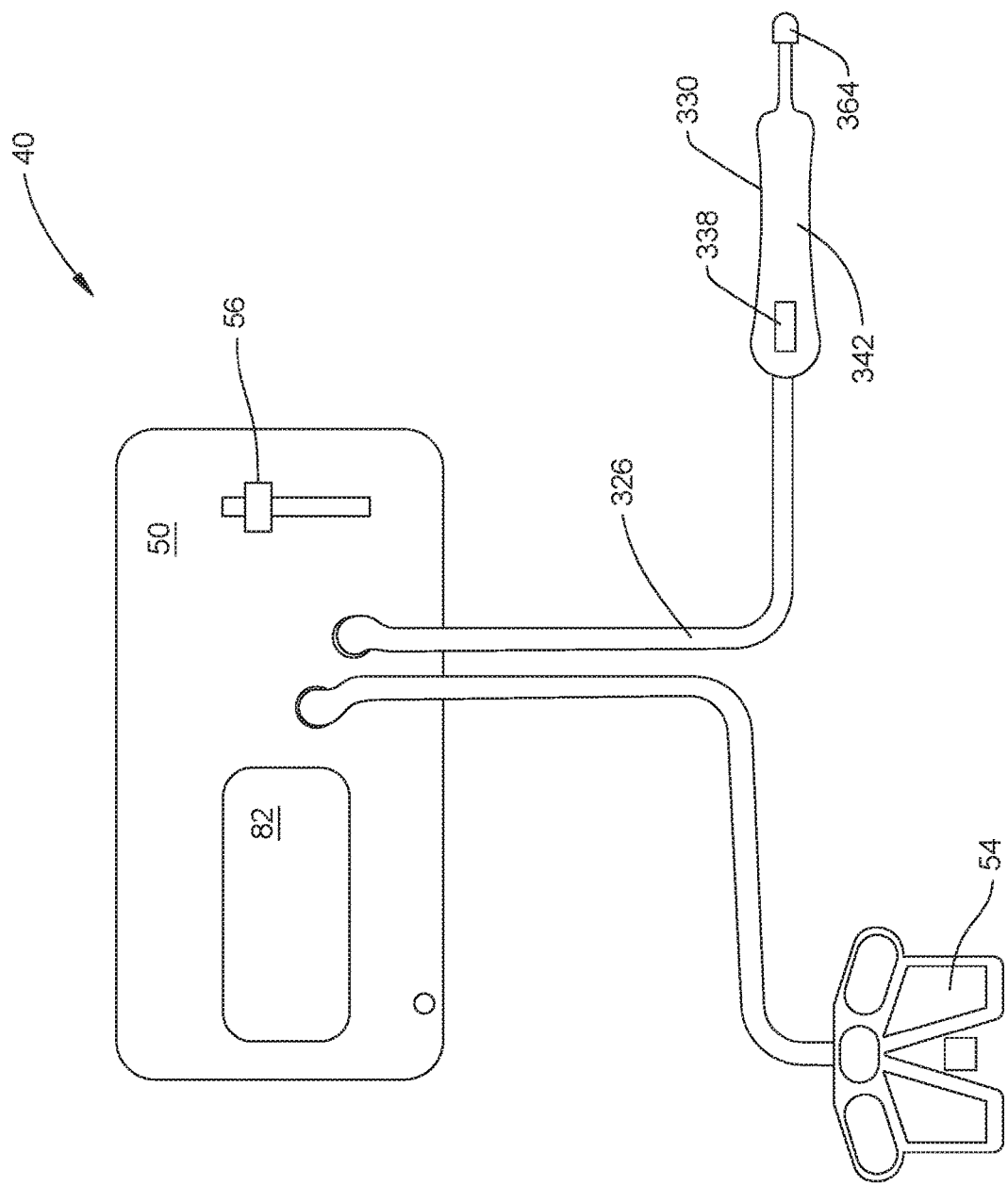
FIG. 1 depicts the basic components of an ultrasonic tool system that includes the features of this invention.

An ultrasonic tool system 40 that includes the features of this invention is now generally described by reference to FIGS. 1 and 2. System 40 includes a handpiece 330. Handpiece 330 includes a body or shell 342 that forms the proximal end of the handpiece. ("Proximal" is understood to mean towards the practitioner holding the handpiece, away from the site to which the handpiece is applied. "Distal" is understood to mean away from the practitioner, towards the site to which the handpiece is applied.)

One or more vibrating piezoelectric drivers 344 (four shown) are disposed inside shell 342. In FIG. 2 the handpiece shell 342 is not seen so the internal components of the handpiece 330 are exposed. Each driver 344 is formed from material that, when a current is applied to the driver, undergoes a momentary expansion or contraction. These expansions/contractions are on the longitudinal axis of a driver 344, the axis that extends between the proximally and distally directed faces of the driver. A pair of leads 346 (FIG. 3) extends away from each driver 344. The leads 346 are attached to the opposed proximally and distally directed faces of the drivers 344. Many, but not all handpieces 330, include piezoelectric drivers 348 that are disc shaped. These drivers 348 are arranged end to end in a stack. Leads 346 are the components of system 40 which the current, in the form of a drive signal, is applied to the drivers 348. Insulating discs 350, one shown, separate adjacent leads 346 connected to adjacent drivers 348 from each other. In FIG. 2, drivers 348 are shown spaced apart from each other. This is for ease of illustrating the components. In practice insulating drivers 344 and discs 350 tightly abut.

A post 336 extends longitudinally through drivers 348 and insulating discs 350. The post 336 extends through the drivers 344 along the collinear longitudinal axes of the drivers. Not seen are through bores internal to the drivers 348 and insulating discs 350 through which the post 336 extends. Post 336 projects outwardly of both the most proximally located driver 40 and the most distally located driver.

A proximal end mass 334 is attached to the proximally directed face of the most proximally located driver 348. The exposed proximal end section of the post 336 is fixedly attached to mass 334. If post 336 is threaded, then mass 334 may be a nut.

A horn 356 extends forward from the distally directed face of the most distally located driver 344. While not shown, an insulating disc 350 may be between the distal driver 344 and horn 356. Horn 356 has a base with a diameter approximately equal to the diameter of the drivers 344. Extending distally forward from the drivers 348, the diameter of the horn 356 decreases. The exposed distal end section of post 336 is affixed to the horn 356. If the post 336 is threaded, the horn base may be formed with a threaded closed end bore (not identified) for receiving the post 336. Handpiece 330 is constructed so that the stack of drivers 344 is compressed between proximal end mass 334 and horn 356.

A tip 360 extends forward from the distal end of the horn 356. A coupling assembly, represented by a collar 358, typically removably holds the tip 360 to horn 356 and therefore the rest of the handpiece 330. The structure of the coupling assembly is not part of the present invention. Tip 360 includes an elongated stem 362. Stem 362 is the portion of the tip that, through the coupling assembly, is attached to the horn 356. Stem 362 extends forward of the handpiece shell 342. Tip 360 is formed to have a head 364 at the distal end of stem 362. Some tip heads 364 have smooth surfaces. Some heads 364 are formed with teeth 366. The geometry of the head 364 is not part of the present invention. Tip head 364 is the portion of the handpiece 330 applied to the site on the patient at which the procedure is performed.

Some tips 360 are provided with teeth designed to be applied directly to hard tissue, bone. When this type of tip is reciprocated, the teeth cut the tissue in the same manner in which a conventional saw blade cuts tissue.

Figure 2:
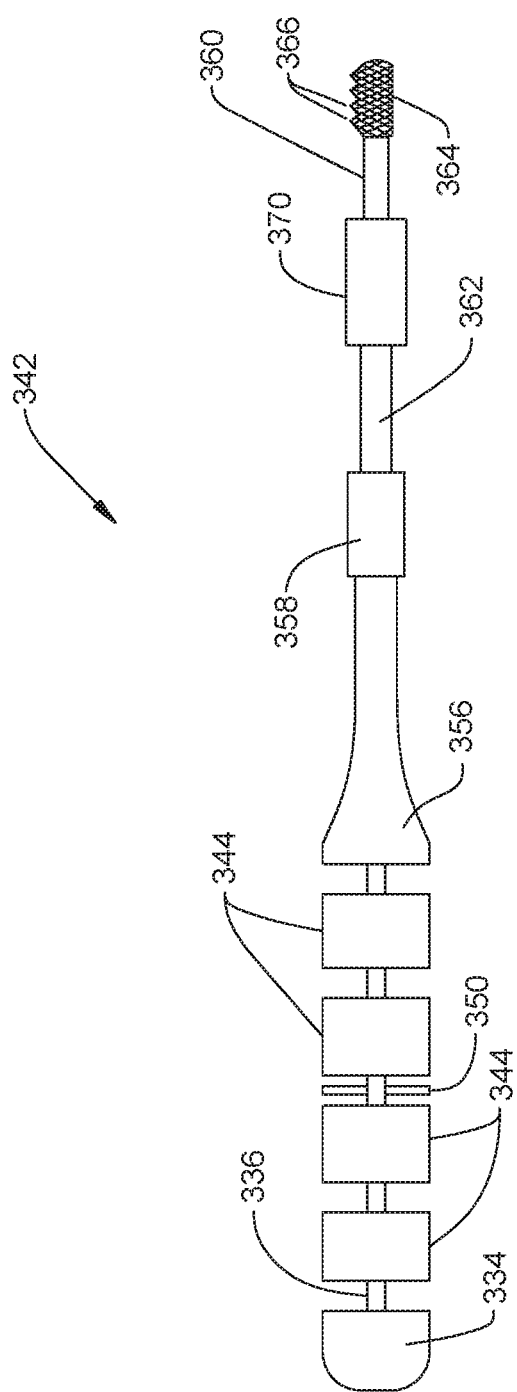
FIG. 2 is a diagrammatic depiction of the mechanical components of the tool, the handpiece, of the system.

A sleeve 370, depicted as a ring in FIG. 2, is typically disposed over tip stem 362. Sleeve 370 typically extends from a location near where the stem is attached to the horn 356 to a location approximately 0.5 cm proximal to the head 364. Collectively the handpiece 330, tip 360 and sleeve 370 are constructed so that the sleeve defines a fluid flow conduit that extends between the outer surface of the tip and the surrounding inner surface of the sleeve. The sleeve 370 also has a fitting (not seen) adjacent the proximal end of the sleeve that extends to this conduit. The conduit is open at the distal end of the sleeve. When the handpiece 330 is in use, irrigating solution is flowed from the sleeve fitting, down the sleeve and discharged adjacent the tip head 364. In some versions of the system, the fluid serves as a medium through which the mechanical vibrations of the tip head are transferred to the tissue. This irrigating solution also functions as a heat sink for the thermal energy developed by the tip head as a consequence of the vibration of the head.

While not seen, the handpiece post 336, horn 356 and tip 360 are often formed with conduits. These conduits collectively define a fluid flow path from the tip head 364 to the proximal end of the handpiece 330. When the handpiece is in operation, suction is drawn through these conduits. The suction draws the irrigating fluid discharged through the sleeve 370 away from the site to which the tip is applied. Entrained in this irrigating fluid are debris generated as a result of the actuation of the tip 360. The suction also draws the tissue towards the tip head. The shortening of the distance between the tip head and the tissue improves the transmission of the mechanical vibrations from the tip head to the tissue.

A handpiece 330 of system 40 able to draw a suction is sometimes referred to as an aspirator or an ultrasonic aspirator.

Handpiece 330 also includes a memory 338. Memory 338, contains data describing the characteristics of the handpiece. Memory 338 may take the form of an EPROM, an EEPROM or an RFID tag. The structure of the memory is not part of the invention. The memory 338 contains data that identifies the handpiece. Memory 338 also contains data describing characteristics of the drive signal that can be applied to the handpiece drivers 348. Most handpieces 330 of this invention include a memory that, in addition to containing data capable of being read are able to store data written to the memory after manufacture of the handpiece. Ancillary components not illustrated are mounted to the handpiece to facilitate the reading of data from and the writing of data to the memory. These components consist of one or more of the following: conductors; exposed contacts/ contact pins; a coil/antenna; or an isolation circuit.

A control console 50 is also part of system 40 of this invention. Control console 50 sources drive signals over a cable 326 to which handpiece 330 is connected. In many but not all versions of system 40, cable 326 and handpiece 330 are assembled as a single unit. The drive signals are applied to the drivers 344. At any given instant, the same drive signal is applied to each driver 344. The application of the drive signals causes the drivers to simultaneously and cyclically expand and contract. A stack of drivers 344 is often between 1 and 5 cm in length. The distance, the amplitude, of movement over a single expansion/contraction cycle of the drivers may be between 1 and 10 microns. Horn 356 amplifies this movement. Consequently, the distal end of the horn 356 and, by extension, tip head 364, when moving from the fully contracted position to the fully extended position, moves typically a maximum of 1000 microns and often 500 microns or less. Some tips 360 are further designed so the longitudinal extension/retraction of the tip stem 362 also induces a rotational movement in the head. This rotational movement is sometimes referred to as a torsional movement. When handpiece 330 is actuated to cause the cyclic movement of the tip, the head 364 is considered to be vibrating.

Figure 3:
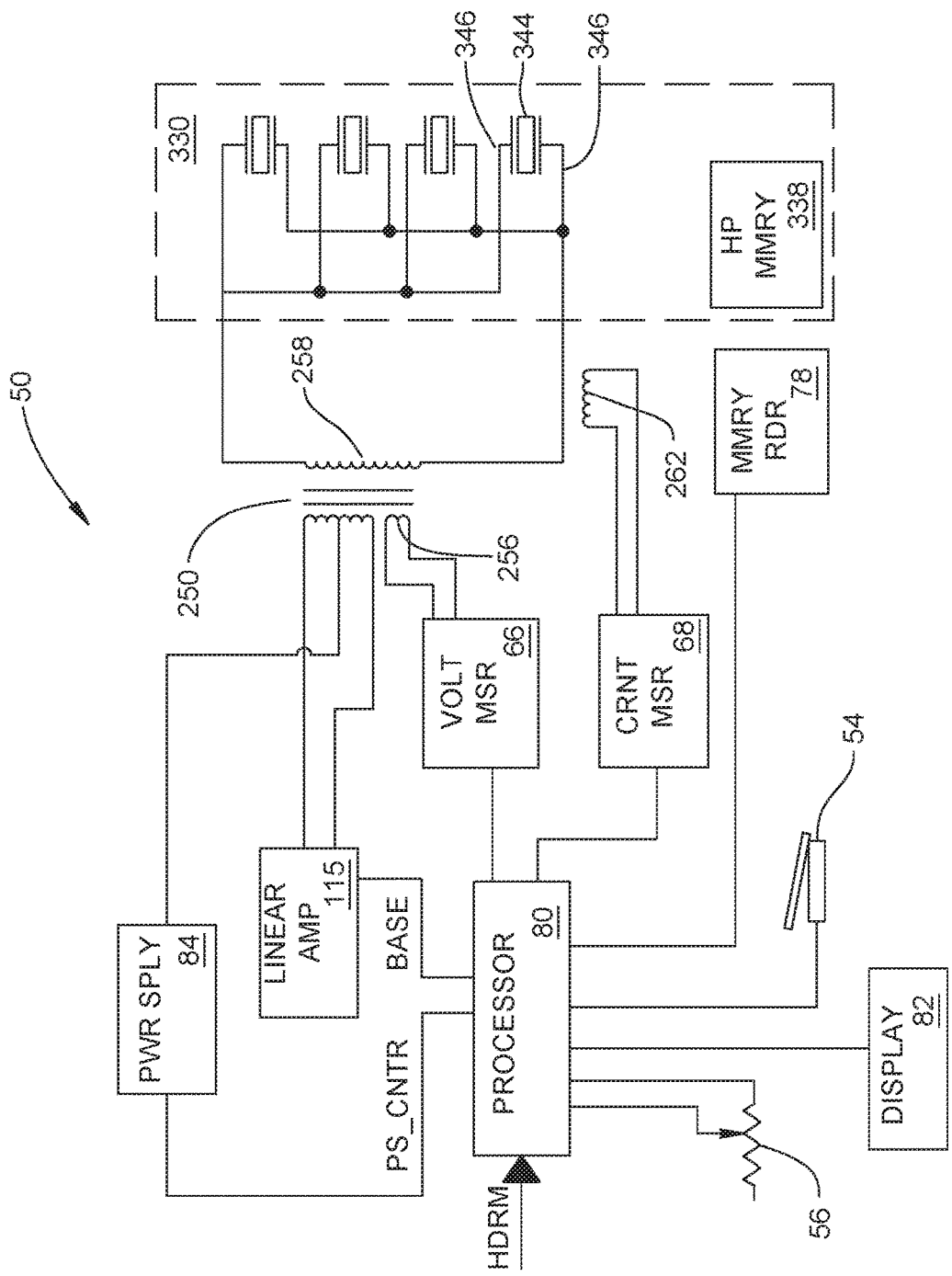
FIG. 3 is a block diagram of the electrical components of both the control console and handpiece components of the system of this invention.

The components internal to the control console 40, generally seen in FIG. 3, includes a power supply 84. Power supply 84 outputs a variable voltage between 25 and 250 VDC. The signal output by the power supply is applied to the center tap of the primary winding of an isolation transformer 250. The potential of the signal output by the power supply 84 is set based on a POWER_SUPPLY_CONTROL (PS_CNTRL) signal applied to the power supply. The opposed ends of the primary winding of the transformer are tied to an amplifier 115. Amplifier 115 applies AC signals that vary in both potential and frequency to the ends of the transformer primary winding. A BASE signal applied to amplifier 115 as a control signal regulates the frequency and potential of the signals output by the amplifier.

The AC signal developed across the primary winding of transformer 250 induces an AC signal across the secondary winding 258 of the transformer 250. This signal across the secondary winding of transformer 250 is the drive signal applied over cable 326 to the handpiece drivers 348.

Transformer 250 includes a tickler coil 256. The voltage of the signal present across tickler coil 256 is applied to a voltage measuring circuit 66. Based on the signal across tickler coil 256, circuit 66 produces a signal representative of $V_S$ the magnitude and phase of the potential of the drive signal across the drivers 344. Given the function and location of tickler coil 256, this component is sometimes referred to as a sense winding. A coil 262, also disposed in control console 50, is located in close proximity to one of the conductors that extends from the transformer secondary winding 258. The signal across coil 262 is applied to a current measuring circuit 68. Circuit 68 produces a signal that represents the magnitude and phase of current $i_S$, the current of the drive signal sourced to the handpiece drivers 344.

The signals representative of the voltage and current of the drive signal applied to handpiece 330 are applied to a processor 80 also internal to the control console 50. Control console 50 also includes a memory reader 78. Memory reader 78 is capable of reading the data in handpiece memory 338. The structure of memory reader 78 complements the handpiece memory 338. Thus, memory reader can be: an assembly capable of reading data in a EPROM or EEPROM or an assembly capable of interrogating and reading data from an RFID tag. In versions of the invention in which the data read from the memory 338 are read over the conductors over which the drive signal is sourced to the handpiece 32, the memory reader 78 may include an isolation circuit. Data read by reader 78 are applied to processor 80.

Connected to control console 64 is an on/off switch. In FIGS. 1 and 3, the on/off switch is represented by a foot pedal 54. The state of pedal 54 is monitored by processor 80. The on/off switch is the user actuated control member that regulates the on/off state of the system 30. In FIG. 1, foot pedal 54 is shown as being part of a foot pedal assembly that includes plural pedals. The added pedals may be used to control devices such as irrigation pump, a suction pump or a light. These supplemental devices are not part of the current invention.

Control console 50 is shown as having a slide switch 56. Like foot pedal 54, the state of switch 56 is monitored by processor 80. Switch 56 is set by the practitioner to control the magnitude of the amplitude of the vibrations of tip head 52. Foot pedal 54 and switch 56 are understood to be general representations of the means of entering on/off and amplitude setting commands to system 40. In some constructions of the system a single control member may perform both functions. Thus, the system may be configured so that when a lever or foot pedal is initially first depressed, the system causes tip head to undergo a vibration cycle that is of relatively small amplitude. As a result of the continued depression of the lever or foot pedal, the control console resets the drive signal applied to the handpiece so as to cause tip head 364 to undergo vibration cycles that are of a larger magnitude.

A display 82 is built into control console 50. The image on display 82 is shown as being generated by processor 80. Information depicted on display 82 includes information identifying the handpiece and possibly the tip; information describing characteristics of the operating rate of the system. Display 82 may be a touch screen display. In these versions of the invention, by depressing images of buttons presented on the display 82 command can be entered into processor 80. Not shown are interface components between the display 82 and the processor 80. These interface components facilitate the presentation of images on the display 82 and the entry of commands into the processor 80.

The processor 80 regulates the outputting of the drive signal from the control console 40. The practitioner-controlled inputs upon which the processor 80 sets the drive signals are the state of the on/off pedal 54 and the state of the slide switch 56. Commands entered through the display 82 may also control the setting of the drive signal. The characteristics of the drive signal are also set based on data read from the handpiece memory 338. The characteristics of the drive signal are also employed by the console as feedback signals that further contribute to the setting of the drive signal. Based on these plural inputs, processor 80 outputs the signals that control the drive signal. These signals are the POWER_SUPPLY_CONTROL signal applied to power supply 84 and the BASE signal applied to amplifier 115.

Figure 4:
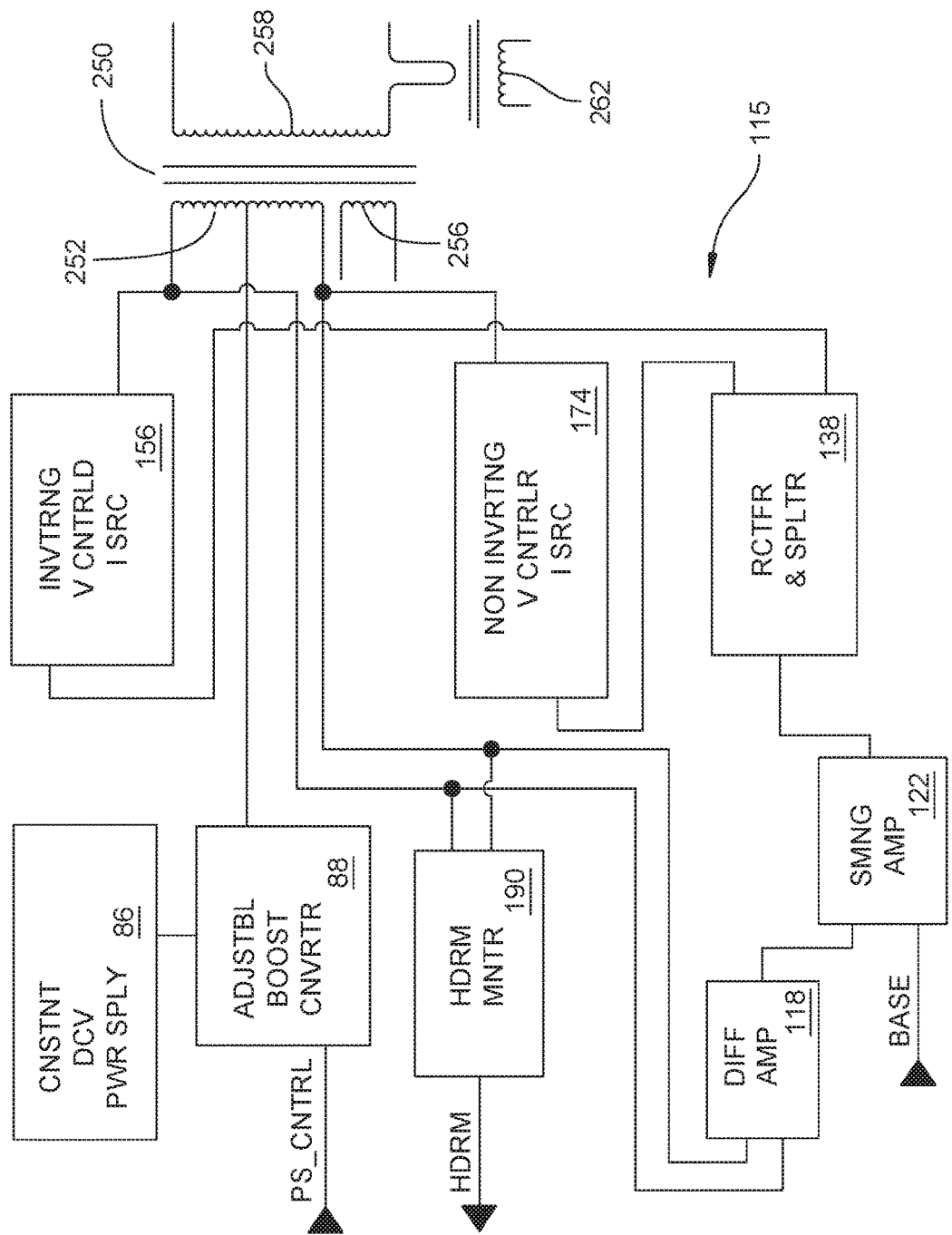
FIG. 4 is a block diagram of the linear amplifier and the DC power supply internal to the control console.

FIG. 4 is a block diagram of sub-assemblies internal to the console that form power supply 84 and amplifier 115. The power supply 84 includes a constant voltage power supply 86. In one version of the invention constant voltage power supply 86 outputs a 24 VDC signal. Not identified are any transformers, rectifiers, filters and voltage regulates that, as part of voltage supply 86, convert the line voltage to the stable DC voltage. Also not identified are voltage sources internal to the console that produce the constant voltage signals needed to run the components internal to the console such as processor 80 and display 82. These voltage sources include the voltage sources that produce the below discussed $V_{cc}$ and $-V_{EE}$ voltages.

The stable DC voltage output by power supply 86 is output to an adjustable boost converter 88, also part of the power supply 84. Boost converter 88 amplifies the potential of the signal from constant voltage power supply 86 to a different potential and outputs the signal as the VAMP signal. In one version of the invention, the boost converter 88 converts the received potential from the constant voltage power supply to a boosted signal between 25 and 500 VDC. In other versions of the invention, the Boost converter 88 produces a variable output signal between 25 and 250 VDC. The POWER_SUPPLY_CONTROL signal output by the processor 80 is applied to the Boost converter 88. The POWER_SUPPLY_CONTROL signal functions as the control input signal upon which the Boost converter 88 sets the potential of the VAMP signal.

Amplifier 115 is a linear amplifier. One of the sub-assemblies of amplifier 115 is the summing amplifier 122. There are two inputs into the summing amplifier 122. A first one of these inputs is the BASE signal from the processor 80. A second input into operational amplifier is a feedback signal the source of which is discussed below. Based on the input signals, the summing amplifier 122 produces a feedback adjusted BASE signal.

The feedback adjusted BASE signal is applied to a rectifier and splitter 138. Rectifier and splitter 138 splits the feedback adjusted BASE signal into positive and negative components. The negative component of the feedback adjusted BASE signal is applied to an inverting voltage controlled current source 156. The positive component of the feedback adjusted BASE signal is applied to a non-inverting voltage controller current source 174. From FIG. 6D it can be seen that the output signal from current source 156 is applied to the gate of a MOSFET 162. The output of current source 174 is applied to the gate of a MOSFET 184.

Current sources 156 and 174 are DC biased. Each current source 156 and 174 is on even when the source does not receive the component of the feedback adjusted BASE signal applied to the source. The drains of MOSFETs 162 and 184 are tied to the opposed ends of transformer primary winding 252.

The signals present at the drains of MOSFETs 162 and 184 are also applied to the inputs of a differential amplifier 118, also part of linear amplifier 115. The output signal from the differential amplifier 118 is the feedback signal is applied to summing amplifier 122.

The signals present at the drains of MOSFETS 162 and 184 are also applied to a headroom monitor 190. Headroom monitor 190 monitors these signals to ensure that there is a sufficient voltage across the MOSFETs 162 and 184 to ensure these MOSFETs are always in saturation. Processor 80 uses the measurements made by the headroom monitor 190 to regulate the voltage of the VAMP signal produced by the boost converter 88.

Figure 5:
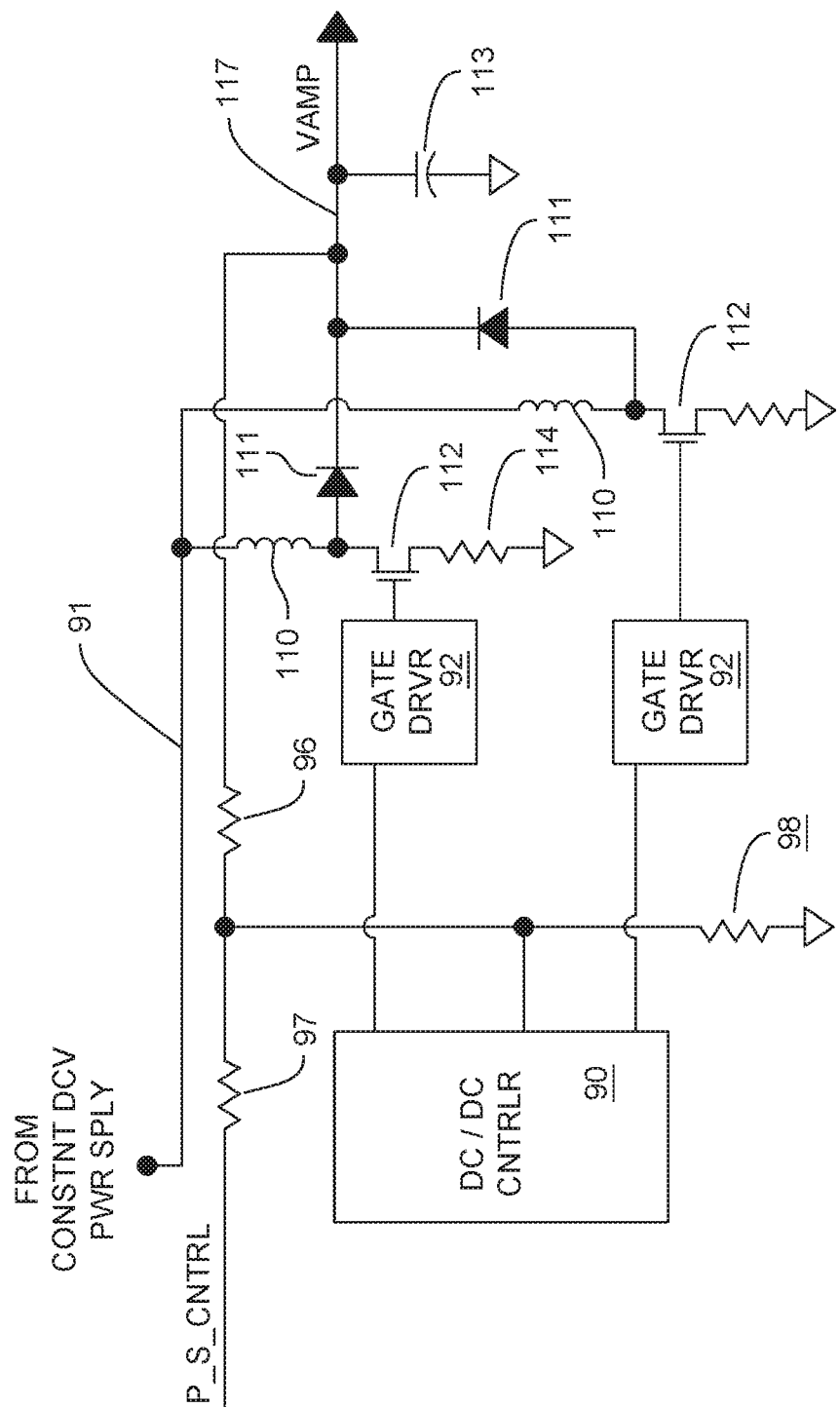
FIG. 5 is a schematic and block diagram of the some of the components integral with the Boost converter of the power supply of the control console.
Figure 15:
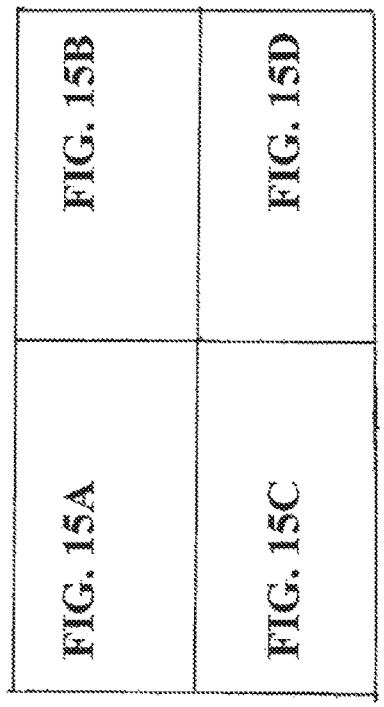
FIG. 15 is an assembly diagram that depicts how

As seen by reference FIG. 5, boost converter 88 includes plural boost circuits. Each boost circuit includes inductor 110. One end of inductor 110 is tied to a constant voltage bus 91. Bus 91 is the conductor over which the constant voltage signal from power supply 86 is applied to the boost converter 88. In some versions of the invention a 24 VDC signal is present on bus 91. The opposed end of the inductor 110 is tied to an n-channel FET 112. The source of the FET 112 is tied to ground through a resistor 114, also part of the boost circuit. Each boost circuit includes a diode 111 the anode of which is connected to the junction of the inductor 110 and FET 112. The gating of each FET 112 is controlled by a DC/DC controller 90. In the illustrated version of the invention, the controller 90 outputs the gate signals to the two illustrated FETs 112. In one version of the invention the LTC3862 Multi-Phase Current Mode Step-Up DC/DC Controller available from Linear Technology Corporation of Milpitas, Calif. can function as the DC/DC controller 90. Each gate signal output by the controller 90 is applied to a gate driver 92. In one version of the invention the TC4422 9 Amp High-Speed MOSFET Driver available from the Microchip Company of Chandler, Ariz. is employed as the gate driver 92.

The cathodes of the plural diodes 111 are connected to a single rail 117. A capacitor 113 is tied between rail 117 and ground.

The signal present on rail 117 is the output signal, VAMP, from the boost amplifier applied to the center tap of the primary winding 252 of transformer 250. The signal present at rail 117 is also applied to ground through series connected resistors 96 and 98. The POWER_SUPPLY_CONTROL signal from processor 80 is applied to through a resistor 97 to the junction of resistors 96 and 98. The signal present at the junction of resistors 96, 97 and 98 is applied to the feedback input of the DC/DC controller 90. Not illustrated are the resistors and capacitors connected to the other pins of the controller 90 to regulate variables such as blanking, duty cycle, operating frequency and phase.

Generally, it is understood that each FET 112 is cyclically gated on and off. When each FET 112 is gated on, there is current flow through the associated inductor 110. When the FET 112 is gated off, the energy stored in the magnetic field around the inductor 110 causes current to flow through the adjacent diode 111. The charge of this current is stored in capacitor 113. During a subsequent turning on of the FET 112 the voltage present at the junction of inductor 110, the diode 111 and FET 112 goes to ground. This process results in an increase in the potential of the signal present on the rail 117 over the potential of the signal applied to the inductors 110.

Plural boost circuits consisting of an inductor 110, a diode 111, a FET 112 and resistor 114 are provided. The plural boost circuits are gated on and off at different times to smooth the voltage of the signal present on rail 117. The DC/DC controller 90 controls the on and off gating of the boost circuits. Controller 90 regulates this gating based on the feedback signal to ensure that the voltage present on rail 117 is at the desired potential.

In FIG. 5, boost converter 88 is shown as having a single DC/DC controller 90 and two boost circuits. This is for ease of illustration and to minimize redundancy. In some versions of the invention, to reduce ripple of the DC signal present on rail 117, the boost converter 88 has more than two boost circuits. In some versions of the invention, the boost converter can have six or more boost circuits. Many known DC/DC controllers are known to only be able to gate two Boost converters. Accordingly, many boost power supplies of this application will also have plural DC/DC controllers 90. Not shown are the connections between these plural DC/DC controllers that regulate when each controller gates the boost circuits attached to the controller. More specifically, the DC/DC controllers are configured so the multiple boost circuits are gated on and off at different times. By providing signals from the plural converters, the voltage present at rail 117 is further smoothed.

Figure 6:
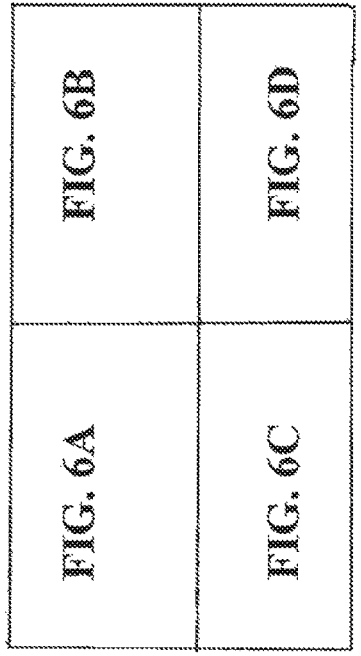
FIG. 6 is an assembly diagram illustrating how FIGS. 6A-6D form a schematic drawing of the linear amplifier of the control console of this invention.
Figure 6A:
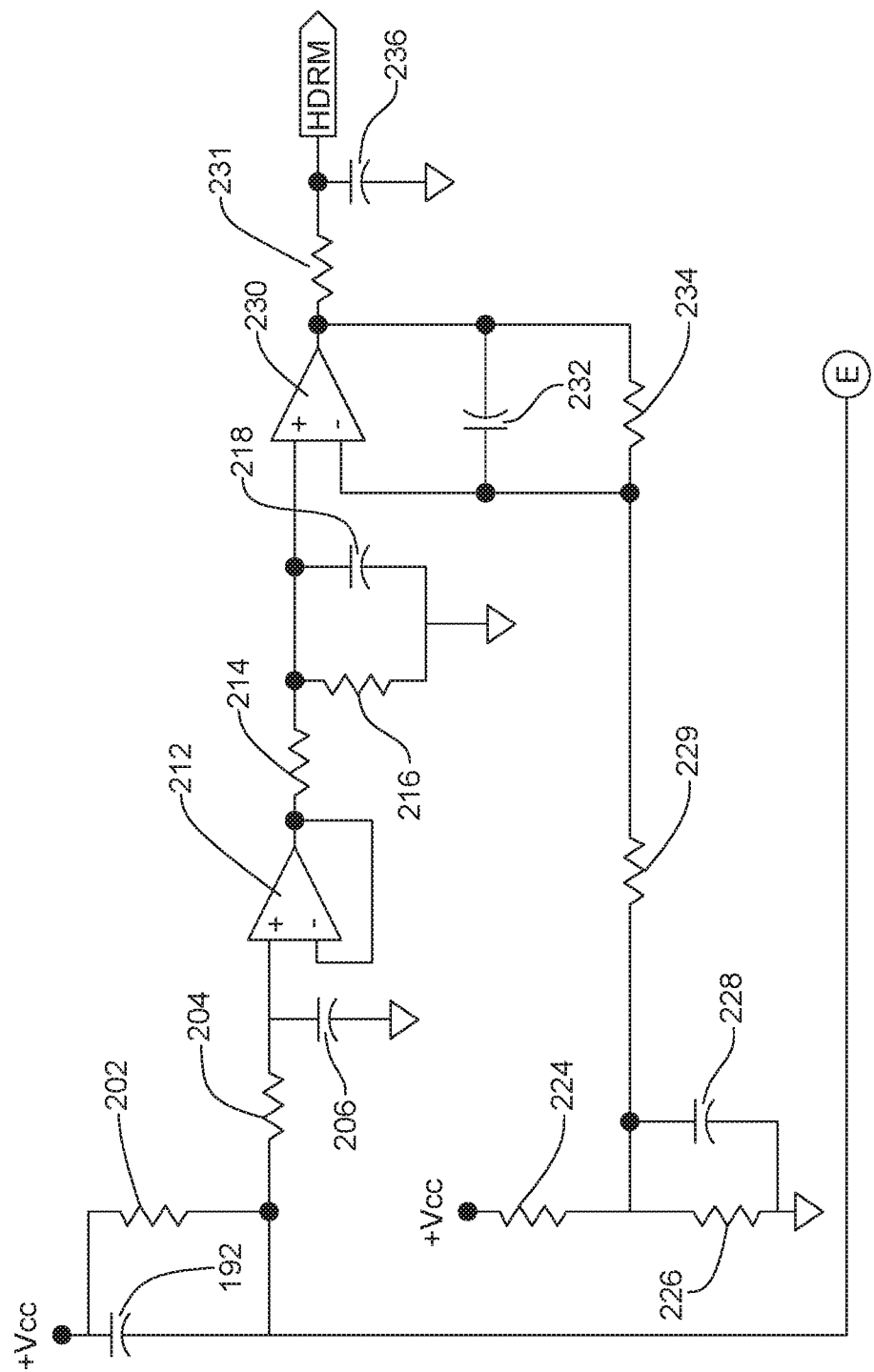
Figure 6B:
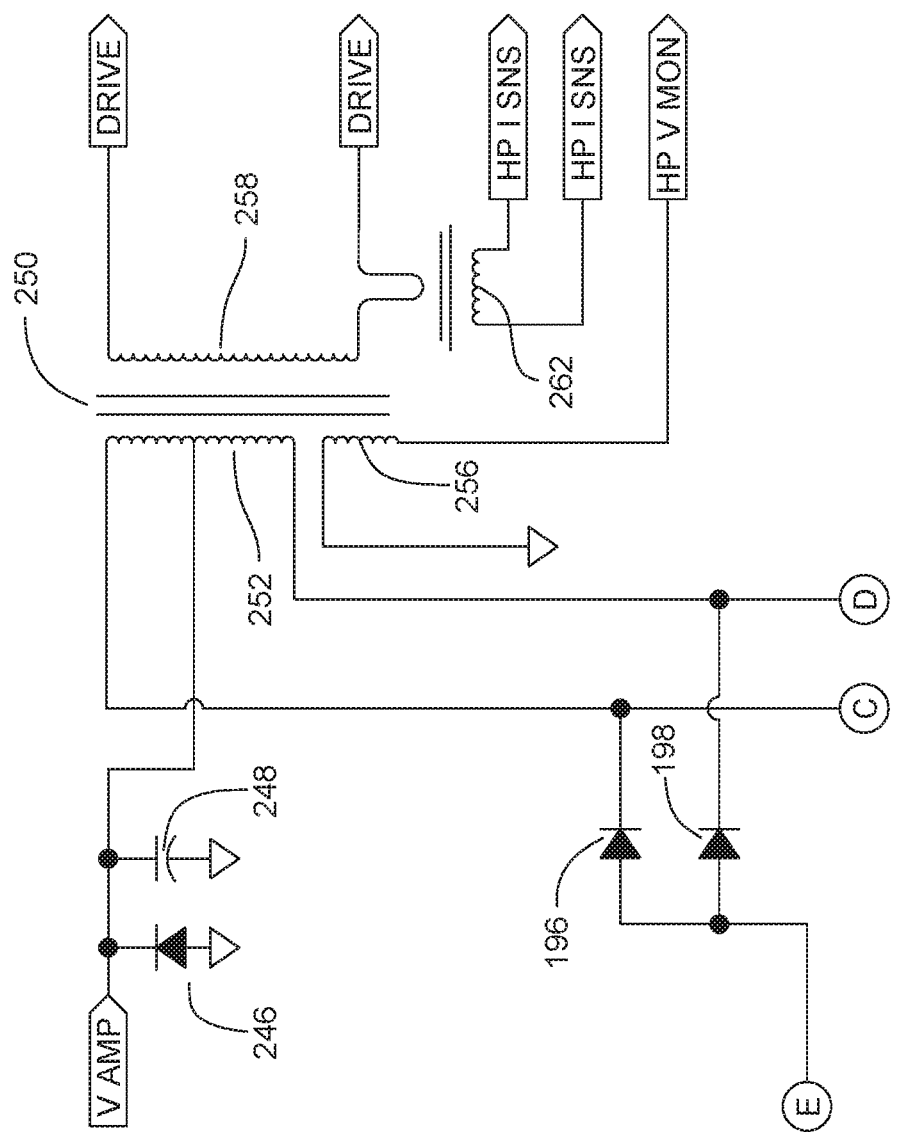
Figure 6C:
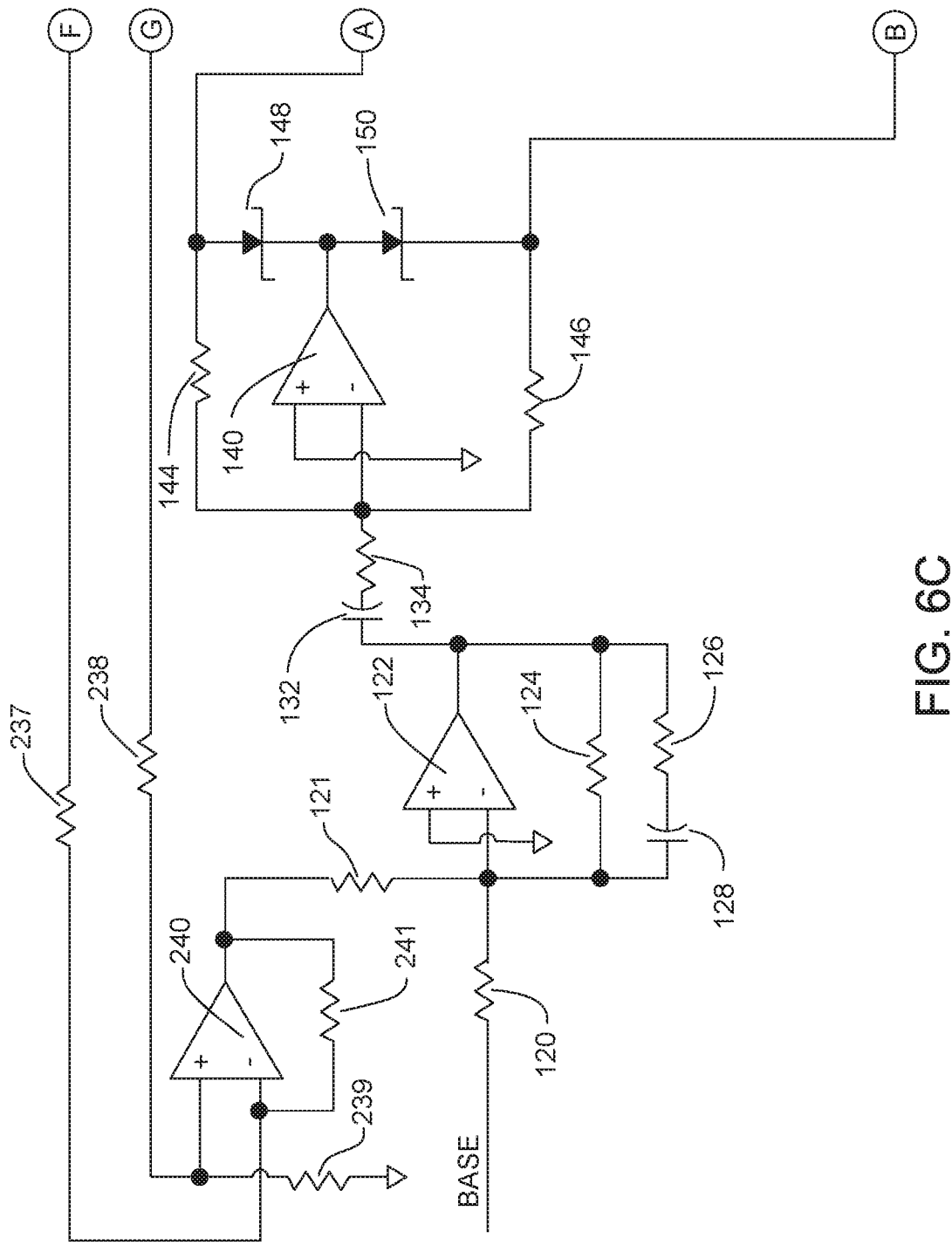
Figure 6D:
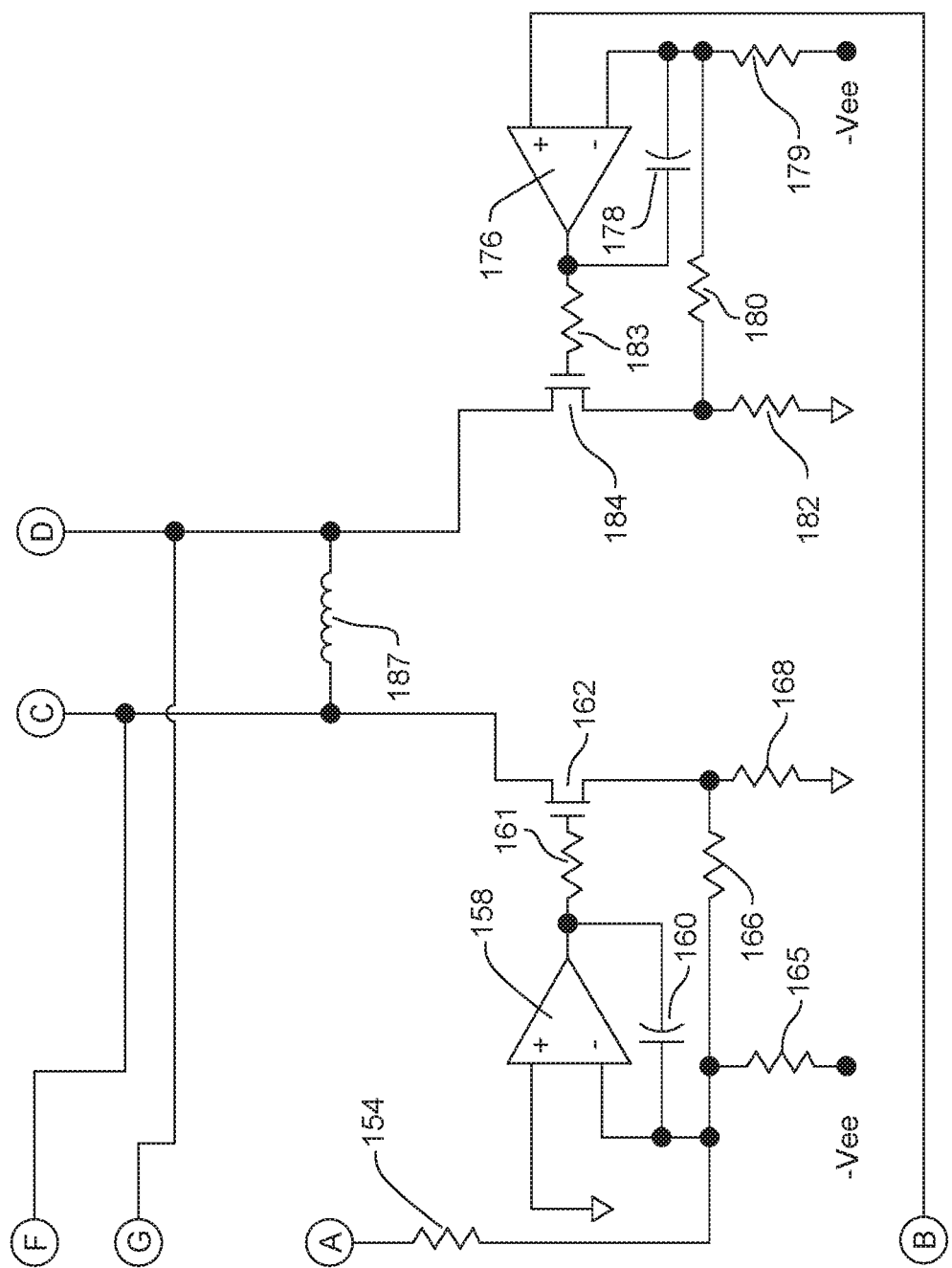

FIGS. 6A-6D, when assembled together, illustrate components of the amplifier 115. Amplifier 122, as seen in FIG. 6C, is an operational amplifier. The BASE signal from processor 80 is applied to the inverting input of the amplifier 122 through a resistor 120. The BASE signal can thus be considered the external control signal amplifier 115 receives to regulate the voltage that appears across the transformer primary winding 252. Also applied to the inverting input of amplifier 122 is the voltage feedback signal from differential amplifier 240. This signal from amplifier 240 is applied to the inverting input of amplifier 122 through a resistor 121. A resistor 124 is tied between the output of amplifier 122 and the inverting input. Also tied across the output of amplifier 122 and the inverting input of the amplifier are a series connected resistor 126 and a capacitor 128. The noninverting input of the summing amplifier 122 is tied to ground.

Summing amplifier 122 is configured as an inverting amplifier. In many versions of the invention this gain is between 4 and 10. The series connected feedback circuit of resistor 126 and capacitor 128 limit the localized gain of amplifier 122 by reducing the gain of the amplifier at high frequencies, typically above 1 MHz. This increases the overall stability of the amplifier circuit. The signal produced by summing amplifier 122 is referred to as the feedback adjusted BASE signal.

The feedback adjusted BASE signal from summing amplifier 122 is applied through a capacitor 132 and resistor 134 to the inverting input of an operation amplifier 140. Operational amplifier 140 is part of rectifier and splitter 138. The non-inverting input of amplifier 140 is tied to ground. The output signal from amplifier 140 is applied to the junction of two series connected diodes Schottky diodes 148 and 150. A resistor 144 is tied between the inverting input of amplifier 140 and the anode of diode 148. A resistor 146 is tied between the inverting input of amplifier 140 and the cathode of diode 150. The signal present at the junction of resistor 144 and diode 148 is the negative component of the feedback adjusted BASE signal. The signal present at the junction of the resistor 146 and diode 150 is the positive component of the feedback adjusted BASE signal.

Rectifier and splitter 138 is configured so the gain out of amplifier 140 is fixed. Typically, the gain is less than 5. Often the gain is unity.

The negative component of the feedback adjusted BASE signal is applied through a resistor 154 to the inverting input of an amplifier 158. Amplifier 158 is part of the inverting voltage controlled current source 156. The non-inverting input of amplifier 158 is tied to ground. A capacitor 160 is tied between the output of amplifier 158 and the inverting input. The output signal from amplifier 158 is also applied through a resistor 161 to the gate of MOSFET 162. The source of MOSFET 162 is tied to ground through a resistor 168. A resistor 166 connects the inverting input of amplifier 158 to the junction between MOSFET 162 and resistor 168. A resistor 165 ties the junction of resistor 154, amplifier 158 resistor 166 to the $-V_{EE}$ voltage source.

The positive component of the feedback adjusted BASE signal is applied to the non-inverting input of amplifier 176. Amplifier 176 is part of non-inverting voltage controlled current source 174. The output signal from amplifier 176 is applied through a resistor 183 to the gate of MOSFET 184. The signal present at the output of amplifier 176 is applied through a capacitor 178 to the inverting input of the amplifier. The inverting input of amplifier 176 is tied to the $-V_{EE}$ voltage source through a resistor 179. The junction of amplifier 176, capacitor 178 and resistor 179 is tied to the source of MOSFET 184 through a resistor 180. A resistor 182 ties the junction of resistor 180 and MOSFET 184 to ground.

Amplifiers 158 and 176 have an identical gain that is fixed. Typically, this gain is less than 5. Often the gain is unity.

The signal present at the drain of MOSFET 162 is applied through a resistor 237 to the inverting input of differential amplifier 240. The signal present at the drain of MOSFET 184 is applied to through a resistor 238 to the noninverting input of differential amplifier 240. (Not shown are capacitors that may be in series between resistors 237 and 238 and the associated inputs into amplifier 240.) The noninverting input of differential amplifier 240 is tied to ground through a resistor 239. Feedback to amplifier 240 is through a resistor 241 tied between the output of the amplifier and the inverting input. The signal present at the output of amplifier 240 is the signal applied through resistor 121 to summing amplifier 122.

An inductor 187 is connected between the drains of MOSFETs 162 and 184. The drains of MOSFETs 162 and 184 are connected to the opposed ends of primary winding 252 of transformer 250.

Inductor 187 is selected to have an inductance that, ideally, if the inductor was connected in parallel across the drivers would form a circuit that has a resonant frequency substantially equal to the resonant frequency of the handpiece. It is understood that the resonant frequencies of the handpieces 330 will vary. The inductance of inductor 187 is fixed. Accordingly, the inductance of the inductor is selected so that if the inductor was tied in parallel across the drivers 344, the resonant frequency of this circuit would be within 50% and more ideally within 25% of the resonant frequency of the handpiece 330. Again, the resonant frequency of the handpiece is understood to be a frequency of the drive signal that, at a given voltage or current, the application of the drive signal at that frequency induces vibrations in the tip that are larger in amplitude in comparison to the application of the same voltage or current at frequency that is off resonance.

While not illustrated, in some versions of the invention, the connection of each MOSFET 162 and 184 is through a current sensing transformer. This current sensing transformer has on one side two primary windings and the opposed sides a single secondary winding. Each MOSFET 162 and 184 is tied to one end of a separate one the primary windings of the current sensing transformer. The opposed end of the primary winding of the current sensing transformer to which MOSFET 162 is connected is tied to a first end of transformer primary winding 252. The opposed end of the primary winding of the current sensing transformer to which MOSFET 184 is connected is tied to the second end of transformer primary winding 252. The signal across the secondary winding of this current sensing transformer thus represents the current sourced by the amplifier. A digitized representation of the signal across the current sensing transform is applied to the processor 80. The processor 80 monitors this signal to determine if an excessive amount of power is being sourced from the amplifier. If the processor 80 determines the console is in this state, the processor takes steps to terminate or reduce the sourcing of power from the amplifier. The processes by which the processor 80 performs this monitoring and so regulates the operation of the console are not part of the present invention.

Figure 7:
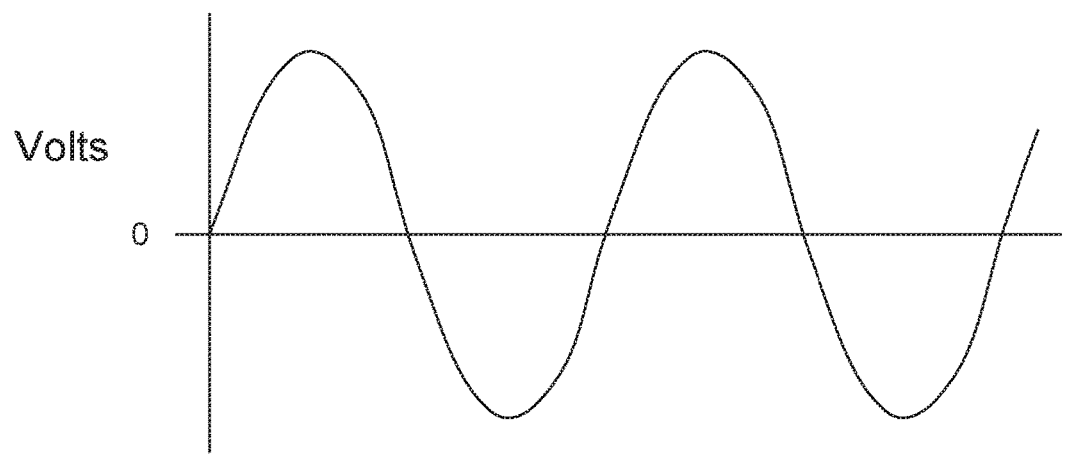
FIG. 7 depicts the waveform present at the output of the operational amplifier of the linear amplifier.
Figure 8A:
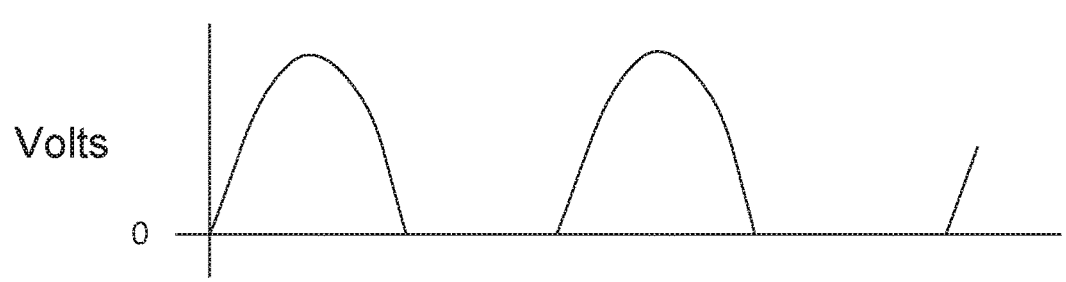
FIGS. 8A and 8B depict the waveforms present at the outputs of the rectifier and splitter of the linear amplifier.
Figure 8B:
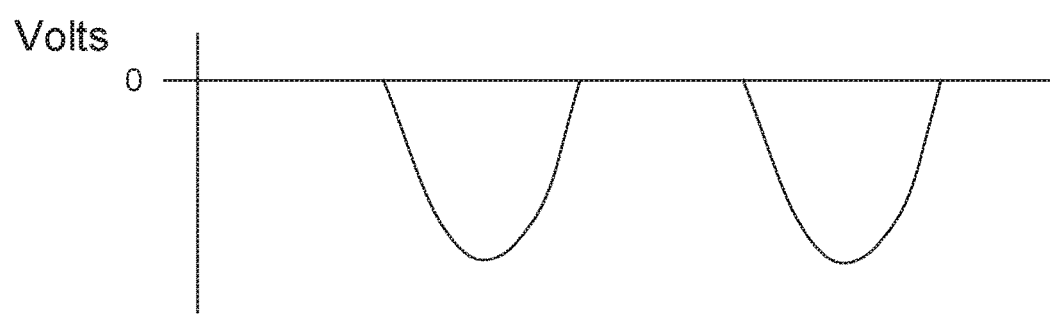

An understanding of operation of linear amplifier 115 is obtained by initial reference to FIGS. 7, 8A and 8B. FIG. 7 is a waveform of the feedback adjusted BASE signal output from summing amplifier 122. Rectifier and splitter 138 splits the feedback adjusted BASE signal into its positive and negative components. FIG. 8A depicts the positive component of the feedback adjusted BASE signal present at the cathode of diode 150. FIG. 8B depicts the negative component of the feedback adjusted BASE signal present at the anode of diode 148.

Figure 9A:
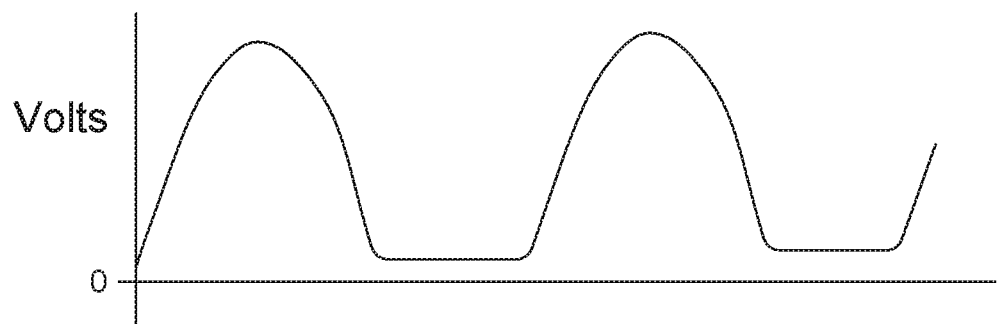
FIG. 9A depicts the waveform of the current produced by a first one of the current sources of the linear amplifier.

The positive component of the feedback adjusted BASE signal is applied to the non-inverting voltage controlled current source 174. The half sinusoidal portions of the waveform seen in FIG. 9A represent that when the input signal applied to current source 174 is above zero volts, the output signal from the current source tracks the input signal. By returning to FIG. 8A it is understood that there are times when the input signal to current source 174 is near zero. It will be recalled that the $-V_{EE}$ signal is applied to the inverting input of amplifier 176. As a consequence of the $-V_{EE}$ signal being so applied to amplifier 176, even when input signal is zero volts, amplifier 176 produces a constant low voltage output signal. In FIG. 9A this is represented by the linear sections of the waveform between the adjacent half sinusoidal sections. These linear portions of the signal are above zero Volts.

Figure 9B:
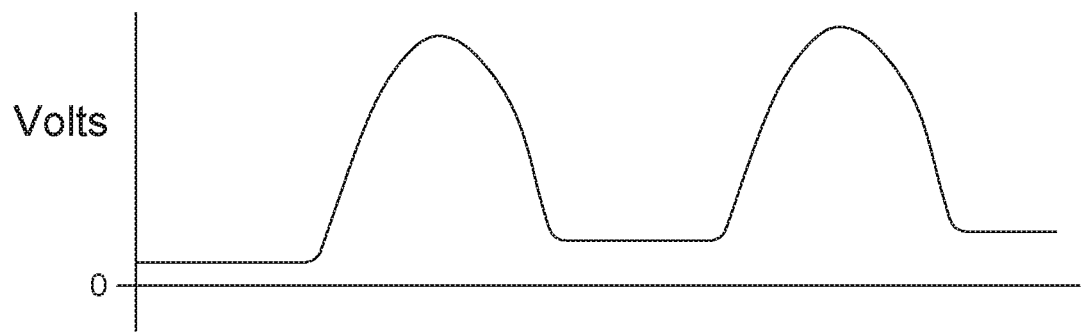
FIG. 9B depicts the waveform of the current produced by a second one of the current sources of the linear amplifier.

The negative components of the feedback adjusted BASE signal are applied to amplifier 158. The half sinusoidal portions of the waveform seen in FIG. 9B represent that these portions of the feedback adjusted BASE signal are inverted and output by amplifier 158. Again it is understood that the $-V_{EE}$ signal is also applied to amplifier 158. This is why, during periods in which the negative components of the feedback adjusted BASE signal are zero, amplifier will output a low level signal. In FIG. 9B this is represented by the linear sections of the waveform between the half sinusoidal sections being at a voltage greater than zero volts.

Figure 10:
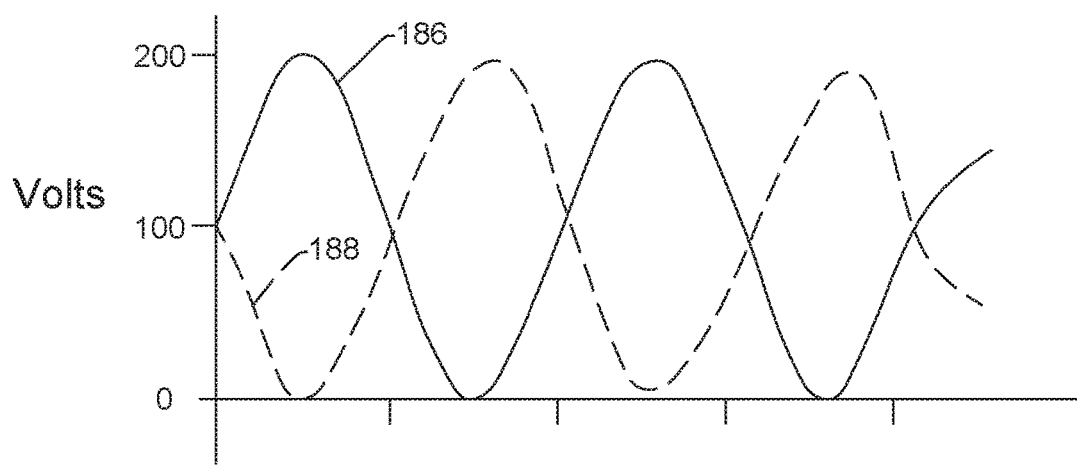
FIG. 10 depicts the voltages present at each end of the transformer primary winding.

The signals applied to the gates of MOSFETs 162 and 184 are therefore applied to the MOSFETs in interleaved time frames. FIG. 10 represents the effects of turning on and turning off of MOSFETs 162 and 184 on the opposed ends of the transformer primary winding 252. The waveforms of this Figure are based on the condition that power supply 84 is applying a 100 VDC signal to the winding center tap. For ease of understanding the operation of amplifier 115, the waveforms of FIG. 10 do not consider the need to ensure that there is a sufficient headroom voltage across the MOSFETs 162 and 184.

Figure 11:
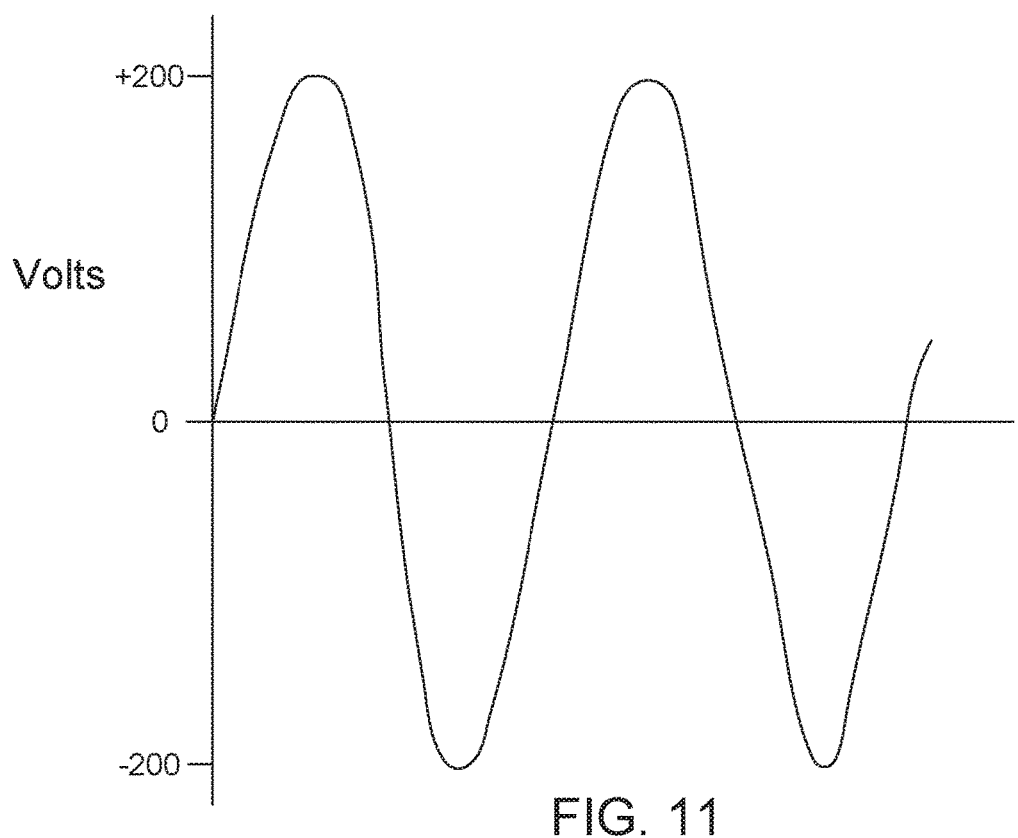
FIG. 11 depicts the voltages present across the transformer primary winding when the voltages of FIG. 10 are present at each end of the winding.

Solid line waveform 186 of FIG. 10 represents the voltage present at the end of the winding 252 to which MOSFET 162 is connected. This is the end of winding 252 at the top of transformer 250 in FIG. 6B. Dashed line waveform 188 represents the voltage present at the end of the winding 252 to which MOSFET 184 is connected. This is the end of the winding at the bottom of transformer 250. During an initial time frame, MOSFET 162 is assumed to be turned off. As a result of the turning on of MOSFET 184, the voltage present at the associated end of primary winding is tied to ground and therefore pulled low. This is represented by dashed line waveform falling from the 100 Volts to near zero. The electric field at this end of the winding essentially collapses. Simultaneously, during this time frame, MOSFET 162 is effectively off. The collapse of the electric field of the end of the winding 252 to which MOSFET 184 is connected induces an increase in the electric field at the opposite end of the winding. Owing to this end of the winding 252 effectively being an open circuit, the voltage at this end of the winding rises. This rise in voltage is essentially equal to the drop in voltage at the opposed end of the winding. Thus as represented by the initial positive going progression of waveform 186, the voltage at this end of the winding rises from 100 V to 200 V. As a consequence of these change in voltage levels at the opposed ends of primary winding the voltage present at the top of winding 252 is 200 Volts more positive than the voltage at the bottom of the winding. In FIG. 11 this is represented by the initial rise of waveform 189 from 0 Volts to 200 Volts.

As MOSFET 184 is turned off, the voltage present at the bottom of the winding 252 rises back to 100 Volts, the voltage present at the center tap. The voltage present at the top of winding 252 drops back to the center tap voltage. The voltage across the winding 252 essentially falls to zero. FIG. 11 this is represented by the initial fall of waveform 189 from 200 Volts to 0 Volts.

During the next time frame, MOSFET 162 is turned on while MOSFET 184 remains off. The turning off of MOSFET 162 connects the associated end of the winding to ground. The voltage present at the top of winding 252 drops from 100 Volts to near ground. In FIG. 10 this is represented by the section of waveform 186 that falls from 100 Volts to essential zero volts. At this time, owing to MOSFET 184 being off, the bottom of winding 252 is effectively an open circuit. The collapse of the field around the top of winding 252 results in the rise of the field around the bottom of the winding. This results in the potential at the bottom of the winding increasing. This is represented the section of waveform 188 that rises from 100 Volts to 200 Volts. As a result in the shift of voltages across the primary winding 252, the top of the winding develops a voltage that is negative with respect to the voltage at the bottom of the winding. In FIG. 11 this is represented by the drop of waveform 189 from 0 Volts to −200 Volts.

After MOSFET 162 is turned on, the MOSFET 162 is turned off while MOSFET 184 remains off. This results in the voltage present at the top of winding 252 rising back to 100 Volts. Simultaneously, the voltage present at the bottom of winding 252 drops back to 100 Voltages. During the moment when both MOSFETs 162 and 184 are effectively off, there is effectively no voltage drop across the winding. This is represented in FIG. 11 by the rise in waveform 189 from −200 Volts back to 0 Volts. Thus this turning on and off of the MOSFETs 162 and 184 causes an AC voltage to develop across the transformer primary winding 252.

The frames then repeat. In some versions of the invention ratio of turns of the secondary winding 258 to the primary winding 252 is between 2 and 10. In more preferred versions the range is between 2 and 5.

In actuality it is understood that only when it is necessary to cause the maximum voltage to appear across the transformer primary winding 252 are the MOSFETs 162 and 184 turned fully on or turned fully off. These MOSFETs 162 and 184 function as active resistors. The varying of the resistances of the MOSFETs by the current sources 156 and 174 is what causes peak to peak voltages to appear across the primary winding that are less than a voltages that are two times the DC voltage present at the center tap.

Figure 12:
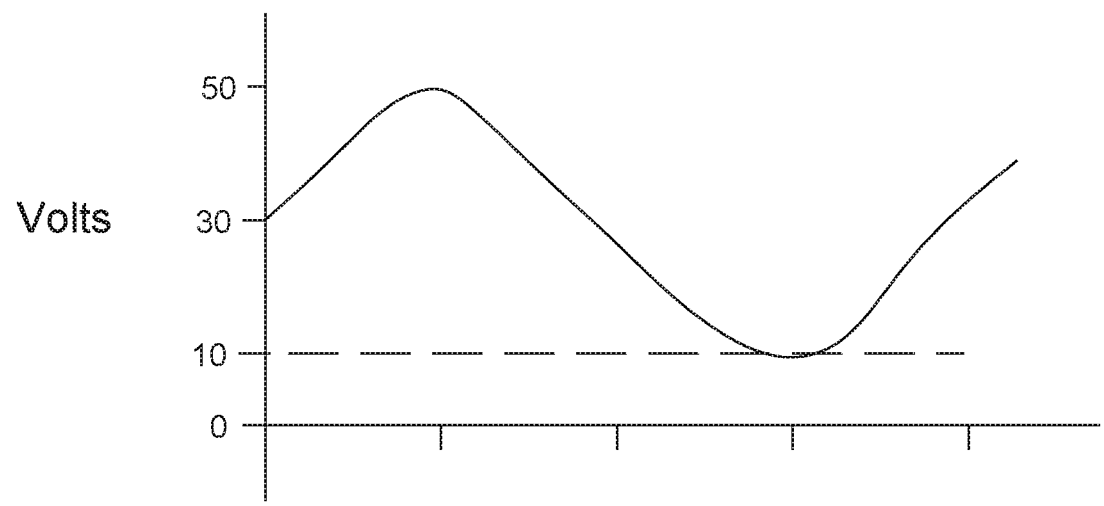
FIG. 12 depicts the voltage present across the transformer primary winding when the minimum voltage is at the headroom voltage.

As discussed above, processor 80, in addition to regulating the characteristics of the BASE signal, also regulates the voltage of the VAMP signal applied to the center tap of transformer winding 252. This is to ensure that, regardless of the voltage present at the ends of the transformer winding 252, there is sufficient but not excessive headroom voltage present at the drains of MOSFETs 162 and 184. The reason this monitoring is performed is understood by first reference to FIG. 12. This Figure represents the voltage present at the one end of transformed winding 252, arbitrarily the top end. More particularly, FIG. 12 represents the voltage present when the center tap voltage is 30 Volts and the MOSFETs 162 and 184 are operated to cause the voltage to oscillate 40 Volts peak to peak. When console 50 is in this state, the minimum drain to source voltage across MOSFET 184, is 10 Volts. For the purposes of understanding the invention, it will be assumed that 10 Volts is the minimum headroom voltage for the particular operating state of the system. This means that, when 10 Volts are applied to MOSFETs 162 and 184 there will be sufficient voltage across the MOSFET to ensure that they are in saturation. This ensures that any changes in the voltage applied to the gate of each MOSFET 162 and 184 will result in the desired proportional change of current flow through the MOSFET.

Figure 13:
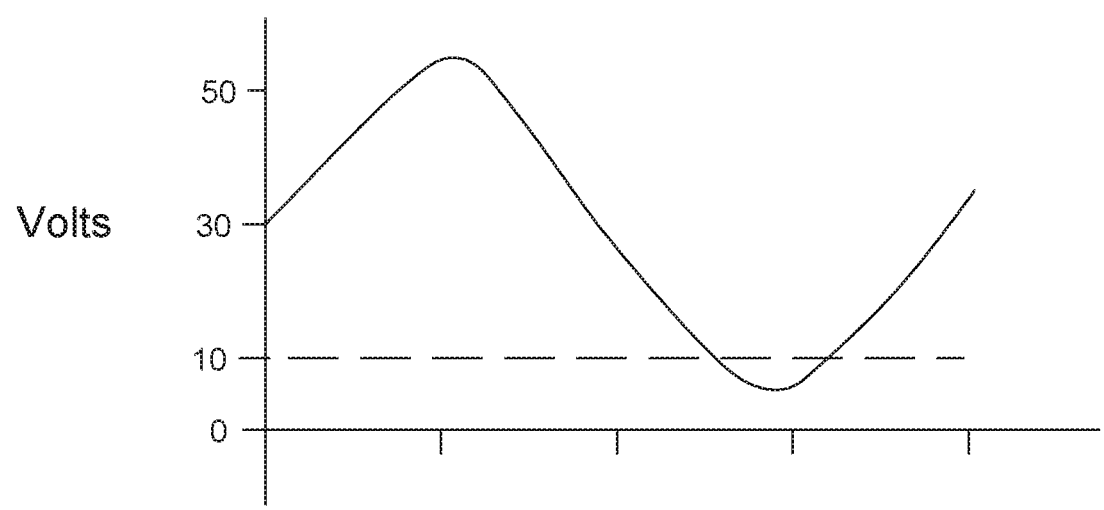
FIG. 13 depicts the voltage present across the transformer primary winding when, owing to an increase in the voltage amplitude, the minimum voltage is below the headroom voltage.

FIG. 13 represents the condition when the voltage at the center tap remains at 30 Volts, but, owing to a need to increase the voltage of the drive signal, MOSFETs 162 and 184 are operated to cause transformer primary winding voltage to oscillate 50 Volts peak to peak. Assuming the voltage level at the center tap remains at 30 Volts, the minimum drain to source voltage drops to 5 Volts. When the voltage across the MOSFET 184 drops to this level, the MOSFET may no longer be in saturation. If MOSFET 184 goes out of saturation, a change in the voltage of the signal applied to the gate may not result in the desired proportional change in current flow through the MOSFET. This would result in the potential present at the associated end of transformer primary winding 252 not being at the potential needed to cause a drive signal of the appropriate potential to appear across the secondary winding 258.

Furthermore, like any amplifier, there are states in which the linear amplifier 115 of this invention will not respond to a change in the potential of the input drive signal with a proportional change in the output of the output signal, here the drive signal. This is especially true when the change in drive signal voltage is based on a change of the load to which the drive signal is applied. The presence of this headroom voltage at the transformer center tap makes it possible for the amplifier's output to rapidly change with a sudden change in load.

Console 50 could be configured so that, at all times, a voltage is presented at the center tap that is high enough so that, even with the greatest swing in winding voltage, the voltages present at the drains of MOSFETs 162 and 184 will always be above saturation level. A disadvantage of so operating the console is that by continually applying high voltages to MOSFETs 162 and 184, a significant amount of the electrical energy applied to the MOSFETs is turned into thermal energy, unwanted heat. To prevent excessive heat loss, processor 80 thus continually adjusts the boost converter 88 to ensure that the VAMP signal output by the converter provides sufficient headroom to the MOSFETs 162 and 184 but is not a level that results in needless heat loss through the MOSFETs.

For the processor 80 to be able adjust the VAMP signal, as well as the BASE signal the processor receives as an input a HEADROOM (HDRM) signal representative of the headroom voltage. The HEADROOM signal is received from the headroom monitor 190 now described by reference to FIGS. 6A and 6B. The headroom monitor 190 includes two diodes 196 and 198. The anodes of both diodes 196 and 198 are connected to the $V_{cc}$ voltage source through a capacitor 192. The cathode of diode 196 is connected to the drain of MOSFET 162. The cathode of diode 198 is connected to the drain of MOSFET 184. A resistor 202 is connected across capacitor 192. The signal present at the junction of capacitor 192, diodes 196 and 198 and resistor 202 is applied through a resistor 204 to the noninverting input of amplifier 212. A capacitor 206 is tied between the noninverting input of amplifier 212 and ground. The output signal from amplifier 212 is tied to the inverting input of the amplifier.

The output signal from amplifier 212 is applied through a resistor 214 to the noninverting input of amplifier 230. A resistor 216 and capacitor 218 are connected in parallel between the noninverting input of amplifier 230 and ground.

Headroom monitor 190 also includes two series connected resistors 224 and 226. The free end of resistor 224 is connected to the $V_{cc}$ rail. The free end of resistor 226 is tied to ground. A capacitor 228 is connected across resistor 226. The signal present at the junction of resistors 224 and 226 and capacitor 228 is applied through a resistor 229 to the inverting input of amplifier 230. A capacitor 232 and a resistor 234 connected in parallel extend between the output of amplifier 230 and the inverting input of the amplifier. The output signal from amplifier 230 is applied to a resistor 231. The end of resistor 234 spaced from amplifier 228 is tied to ground through a capacitor 236. The signal present at the junction of resistor 234 and capacitor 236 is the HEADROOM signal representative of the $V_{DS}$ voltages across MOSFETs 162 and 184.

Headroom monitor 190 does not monitor the $V_{DS}$ voltages directly. Instead, the headroom monitor 190 monitors the voltage present at the drains of the MOSFETs 162 and 184 to ground. For MOSFET 164 this is the voltage across the MOSFET and resistor 168. For MOSFET 182 this is the voltage across the MOSFET and resistor 182. Current flows across diode 196 or 198 when the voltage present at the drain of the associated MOSFET 162 or 184, falls below the potential of the $V_{cc}$ signal. When this condition exits, the potential of the signal applied through resistor 204 to the noninverting input of amplifier 212 falls. The output signal from the amplifier 212 undergoes a like drop. This results in a like drop in the output signal from amplifier 228 and by extension a drop in the voltage of the HEADROOM signal.

By selectively setting the resistances of resistors 224 and 226, the potential of the HEADROOM signal relative to the actual headroom voltage across the MOSFETs 162 and 184 can be selectively set. In one version of the invention resistors 224 and 226 are selected so that when the potential of HEADROOM signal is zero volts, the voltage present at the MOSFET drains is a specific voltage somewhere between 8.5 and 10.5 Volts.

The VAMP signal from the boost converter 88 is applied to the center tap of primary winding 252 of transformer 250. A single capacitor 248 is also shown connected between the conductor over which the VAMP signal is applied to transformer 250. Capacitor 248 represents the filtering of the VAMP signal to minimize the AC components of the signal.

Not shown is a relay that may be in line with the conductor over which the VAMP signal is applied from the Boost converter 88 to the transformer center tap 252. This relay is turned on by the processor after diagnostic checks that are part of the process of readying the system indicate that no faults were detected. The process of performing these diagnostic checks is not part of the present invention. When the relay is present a reverse biased diode is also connected between the bus over which the VAMP signal is applied to the transformer center tap. This diode protects the console when the relay is opened.

In FIG. 6B, the opposed ends of the transformer secondary winding 258 are the source of the drive signal applied to the handpiece drivers 344. One end of tickler coil 256 is tied to ground. The HPVMON signal present at the opposed end of the tickler coiler 256 is the signal representative of the voltage of the drive signal $V_S$. The HPVMON signal is the signal applied to the voltage monitor 66. Internal to the console 40, one of the conductors that extends from the transformer secondary winding 258 is shown in close proximity to coil 262. The signal across coil 262, the HPISNS+ and HPISNS− signals of FIG. 6B, is the signal representative of the drive signal current $i_S$. The HPISNS+ and HPISNS− signals are the signals applied to the current monitor 68. Based on the HPISNS+ and HPISNS− signals, current monitor 68 produces a representation of current $i_S$.

Figure 14:
FIG. 14 depicts types of data stored in the memory internal to the handpiece.

To facilitate operation of system 40, memory 338 internal to the handpiece is loaded with data during the assembly of the handpiece. These data, as represented by field 372 of FIG. 14, include data identifying the handpiece 330. These data are useful for verifying that the console 50 is able to apply a drive signal to the handpiece. Data in field 372 may also indicate the type of information regarding the handpiece that is presented on console display 82. Field 374 contains data indicating the capacitance $C_O$ of the stack of drivers 348. Driver capacitance can be determined by analysis during the process of assembling the handpiece 330. Often the sum of the capacitance of the drivers 348 is between 500 to 5000 pF. Data regarding the maximum current that should be applied to the handpiece, current $i_S^{MAX}$, are contained in a field 376. Current $i_S^{MAX}$ is often less than 1 Amp peak and more often 0.5 Amp peak or smaller. Field 378 contains data indicating current $i_M^{MAX}$, the maximum equivalent of current that should be applied mechanical components of the handpiece. Current $i_M^{MAX}$ is typically 0.25 Amps peak or less. The maximum potential of the drive signal, voltage $V_S^{MAX}$, are stored in field 380. Voltage $V_S^{MAX}$ is typically 1500 Volts or less AC peak.

Also stored in handpiece memory 338 are data indicating the minimum and maximum frequencies of the drive signal that should be applied to handpiece 330. The minimum frequency, stored in field 382, is typically the minimum frequency of the drive signal that can be sourced by the control console. The maximum frequency of the drive signal, stored in field 384, is typically between 5 kHz and 40 kHz greater than the minimum frequency.

Field 386 contains coefficients for filtering the signals output by processor 80. Field 388 contains data regarding any step limits associated with increasing the magnitude of the potential of drive signal applied to the handpiece. It should be understood that the data in fields 372, 376, 378, 380, 382, 384, 386 and 388 like the data in field 374, are stored in the handpiece memory 58 as part of the process of assembling the handpiece.

Handpiece memory 338 also contains field 390 as a use history field. Control console 50, during use of the handpiece, writes data into field 388 so as to provide a log of the operation of the handpiece.

FIGS. 15A-15D, when assembled together, provide a view of the processes run on processor 80 to regulate the drive signal output by the console 50 to the handpiece 330. In brief, it should be understood that the objective is for the console 50 to output a drive signal at the frequency and voltage that results in the desired cyclical expanses and contractions of the handpiece drivers 344. The BASE signal and the POWER_SUPPLY_CONTROL signals are the control signals are output by the processor 80 to cause the other components internal to the console 50 to output the target drive signal. Processor 80 generates the BASE signal. Amplifier 115 produces a feedback adjusted BASE signal that is a function of the BASE signal and the signal produced by the amplifier. This feedback adjusted BASE signal is at a frequency and potential that results in the amplifier 115 causing a signal to appear across the transformer primary winding 252. The specific signal the amplifier 115 causes to appear across the transformer primary winding 252 is a signal that causes the target drive signal to be induced across the secondary winding 258.

Processor 80 outputs a POWER_SUPPLY_CONTROL signal that ensures that the potential VAMP power supply 84 applies to the center tap of transformer primary winding 252 is at a level that results in a sufficient but not excessive headroom voltage appearing at the drains of MOSFETs 162 and 184.

To generate the BASE and POWER_SUPPLY_CONTROL signals, processor 80 continually executes three control loops. A first control loop sets the frequency of the BASE signal. A second control loop sets the voltage of the BASE signal. The outputs of these two control loops are combined to produce the BASE signal. The third control loop generates the POWER_SUPPLY_CONTROL signal.

An output from the second control loop, the control loop used set the voltage of the BASE signal, is an input into the third control loop.

The gains of amplifiers 118 and 122, rectifier and splitter 138 and current sources 156 and 174 are fixed. Therefore, the voltage of the signal applied across the transformer primary winding 252 is proportional to the voltage of the BASE signal. The frequency of the BASE signal is the frequency of the signal present across the transformer primary winding 252. Accordingly, in the following descriptions of the modules run on processor 80, the voltage and frequency of the BASE signal are used as the input variables representative of these characteristics of the signal present across the primary winding 252. It should also be understood that the frequency of the BASE signal is the frequency of the drive signal present across transformer secondary winding 258. This is why the modules run on the processor are able to use the frequency of the BASE signal as an input variable representative of the frequency of the drive signal.

One of the modules of the first control loop is the frequency tracking calculator 292. Frequency tracking calculator 292 determines the characteristics of the drive signal presently applied to the handpiece drivers 348. In one version of the invention, frequency tracking calculator 292 determines the ratio of $i_O$ the current flowing through the handpiece drivers 344 to $i_M$. Variable $i_M$ is a mathematical equivalent of current applied to the mechanical components of the handpiece 330. The mechanical components of the handpiece are the components of the handpiece that, in response to the application of the drive signal, vibrate. These components include: the proximal end mass 334; post 336; drivers 344; horn 356, including the coupling assembly; and the tip 360. Drivers 344 are included as part of these components because the drivers, since they vibrate, are part of the vibrating mechanical assembly of this invention. Sleeve 370 is typically not considered one of these components. This is because, while the sleeve 370 vibrates, the sleeve is not part of the vibrating system. More specifically, sleeve 370 can be considered a component that places a load on the vibrating system.

Current $i_O$ through drivers 344 is a function of $C_O$, the capacitance of the drivers, the voltage across the drivers and $\omega$, the radian frequency of the drive signal. More specifically, $$i_O = j\omega C_O V_S \quad (1)$$

The voltage across the drivers, $V_S$, is the voltage of the drive signal. The equivalent of current $i_M$ through the mechanical components of the handpiece 330 is the difference between $i_S$, the current applied to the handpiece 330. The equivalent of current $i_M$ is thus determined according to the equation:

$$i_M = i_S - j\omega C_O V_S \quad (2)$$

Currents $i_S$ and $i_O$, the equivalent of current $i_M$ and voltage $V_S$ are understood to be vectors each of which has a magnitude component and a phase component.

Frequency tracking calculator 292 therefore receives as inputs: the digitized representation of $V_S$ as measured across tickler coil 256 and the digitized representation of $i_S$ based on the potential across coil 262. A third input into the calculator 292 is capacitance $C_O$ from field 374 of handpiece memory 338. A fourth input into calculator 292 is the present frequency of the drive signal. Based on these variables, the frequency tracking calculator 292 determines the ratio of current through the drivers to the equivalent of current through the mechanical components of the handpiece according to the following formula:

$$-\operatorname{Re}\left\{\frac{j\omega V_s C_O}{i_s - j\omega V_s C_O}\right\} \quad (3)$$

The ratio output by calculator 292 is applied to base frequency controller 294. The base frequency controller 294 compares the ratio of Equation (3) to a fixed value, arbitrarily F. In practice, F can be between −100 and 100. It should be understood that this range is exemplary, not limiting. There are a number of constructions of the invention wherein F is between −1.0 and 1.0. If the system is intended to apply a drive signal that matches the mechanical resonance of the handpiece F is typically zero. Value F is typically constant throughout a single use of system 40.

Controller 294 thus performs the following evaluation:

$$-\operatorname{Re}\left\{\frac{j\omega V_s C_O}{i_s - j\omega V_s C_O}\right\} \approx F \quad (4)$$

Generally, if the ratio is within +/−0.1 of F, more often within +/−0.05 of F and, ideally, within +/−0.01 of F, the present drive frequency is considered to be close enough to the target drive frequency that the controller does not need to adjust this frequency.

If the evaluation of Equation (4) tests false, controller 294 generates a new frequency for the drive signal. This new frequency is a frequency that should, during a subsequent evaluation of Equation (4) result in the evaluation testing true. The new frequency is based in part of the present frequency of the drive signal. The present frequency of the drive signal is understood to be the frequency of the drive signal previously calculated by controller 294 in the last cycle of the frequency calculation process. This is why, in FIG. 15B the previously calculated drive frequency is shown as being feedback to base frequency controller 294. This previously calculated value drive frequency is also depicted as being fed back to frequency tracking calculator 292. Calculator 292 uses this previous calculated value BASE signal frequency as the input variable $\omega$, the radian frequency of the drive signal.

A detailed analysis of the basis for Equations (1), (2), (3) and (4) is contained in PCT Pub. No. WO 2015/021216 A1/US Pat. Pub. No. 2017/0071621 A1, the contents of which are explicitly incorporated herein by reference.

The new frequency for the drive signal is generated using a proportional, integral and derivative (PID) control loop. While not shown in FIG. 15B, the coefficients for the PID loop may be based on coefficients from handpiece memory field 388. The new frequency for the drive signal generated by base frequency controller 294 is applied to a base signal generator 310. The minimum and maximum limits of the drive frequency are based on the data in fields 382 and 386 in the handpiece memory 338.

The second control loop includes an equivalent of current calculator 296. The equivalent of current calculator 296 determines the equivalent of current for the mechanical components of the handpiece 330. This is the equivalent of current calculated according to Equation (2). To distinguish between the below discussed target equivalent of current, this calculated equivalent of current is referred to as variable $i_M^{CALC}$. From the above it should be understood that the equivalent of current is calculated by the frequency tracking calculator 292. Accordingly, in some versions of the invention, there is no calculator 296. In these versions of the invention, the equivalent of current $i_M^{CALC}$ calculated by the frequency tracking calculator 292 as a consequence of the determination of the frequency tracking ratio is applied to the next module of the control loop that sets the potential of the drive signal, the base voltage controller 306.

A second input into the base voltage controller 306 is a value representative of the target equivalent of mechanical current, $i_M^{TARG}$. Target equivalent of mechanical current $i_M^{TARG}$ comes from a calculator 305, another module run on processor 80. The input into calculator 305 is the signal representing the practitioner desired operating rate for the handpiece 330. This operating rate is based on the practitioner's setting of switch 56 of the equivalent foot pedal. Calculator 305, based on the input signal supplied by the switch, generates the value for the target equivalent of mechanical current $i_M^{TARG}$. A second input calculator 305 employs to generate the target equivalent of mechanical current $i_M^{TARG}$ is the frequency of the drive signal. Calculator 305 employs the frequency of the BASE signal previously calculated by the base frequency controller 294 as the variable representative of drive signal frequency.

The base voltage controller 306 is the module that generates the next value of the voltage for the BASE signal. Base voltage controller 306 first determines the difference between the target equivalent of current $i_M^{TARG}$ and the current calculated equivalent of current $i_M^{CALC}$. Based on the difference between these two values, controller 306 then, if necessary, resets the value of the voltage of the BASE signal. This is because the voltage of the BASE signal is the variable that causes a drive signal having the voltage necessary to foster the target equivalent of current to appear across the transformer secondary winding 258. Controller 306 operates a PID control loop to determine the new value of the voltage of the BASE signal. The coefficients for the control loop come from field 386 of handpiece memory 338.

In theory, the base voltage controller 306 should generate signals indicating the newly adjusted potential for the BASE signal based on a conventional control loop such as a PID control loop.

It is understood that the rate of change of BASE signal may further be governed by variables such as the ability of the linear amplifier 115 to rapidly ramp up the drive signal and the handpiece drivers 344 ability to respond to a rapid change in drive signal voltage. Voltage controller 306 is further understood to limit changes in the voltage level of the BASE signal based on these variables. The voltage step limiting variables that are specific to the handpiece are based on data read from field 388 of the handpiece memory 338 when system 40 is initially configured for use. The voltage step limiting variables specific to the console are loaded into the processor 80 during assembly of the console 50.

In practice, other factors affect the ability of the amplifier to increase the voltage level of the drive signal applied to the handpiece drivers 344. These factors include: the voltages present on MOSFETs 162 and 184; the maximum current that can be drawn from the transformer 250; and the maximum voltage of the drive signal that should be applied to the handpiece drivers 344. A voltage limiter 304, another control module run on processor 80, selectively generates commands that limit increases in the commanded voltage level for the BASE signal that is output by voltage controller 306.

Voltage limiter 304 selectively limits the magnitude of the voltage of the BASE signal as well as the rate of change of the voltage of the BASE signal based on a number of input variables. One variable upon which the voltage limiter 304 may determine it is necessary to limit the voltage of the BASE signal is that it would result in a signal appearing across the transformer secondary winding 258 that is in excess of the designed maximum voltage. Often this value is fixed. In some versions of the invention this voltage is at least 1000 Volts peak and more preferably at least 1250 Volts peak. In still other versions of the invention, this voltage can vary. The primary reason this voltage could vary is that the characteristics of the handpiece 330 are such that, in some operating states, the handpiece could draw an excessive amount of current from the console 50.

Accordingly, in some versions of the invention, processor 80 runs a full scale voltage calculator 298. Inputs into calculator 298 are handpiece driver capacitance $C_O$ and the frequency of the drive signal. Again, it should be understood that the frequency of the BASE signal is used as a substitute for the frequency of the drive signal. Collectively, these values may indicate that the if the drive signal applied to the handpiece 330 reaches a certain potential, the impedance of the drivers is such that they will draw more current than the console 50 should provide. In general, the handpiece may be in a state in which there is potential for excessive current draw by the drivers 344, when the drivers have a relatively low capacitance and the drive signal is at a relatively high frequency.

Calculator 298 is a second module that uses as an input variable the previously calculated frequency of the BASE signal. A second variable into calculator 298 is driver capacitance $C_O$. Again, handpiece driver capacitance $C_O$ is understood is loaded to processor 80 during the initialization of the system. As a result of this monitoring, calculator 298 may determine that the handpiece drivers 344 are entering a state in which an increase in the voltage of the drive signal will result in excessive current draw from the console 50. If calculator 298 determines that system 30 is in this state, the calculator generates an instruction to the voltage limiter 304 indicating that the maximum voltage that should appear across the transformer secondary winding 258, the maximum voltage that should be output by the console 50, is a level less than the default maximum voltage. In some versions of the invention, calculator 298 actually determines the maximum voltage that should be allowed to develop across the transformer primary winding 252.

Voltage limiter 304 also receives from the voltage controller 306 data indicating the voltage level for the BASE signal determined in the previous cycle of calculations used to generate the BASE signal. This voltage is used as the input variable for determining the present input voltage across primary winding 252. Given that the ratio of the voltage across the secondary winding 258 relative to the primary winding is fixed, the voltage of the previously calculated BASE signal is also used as a variable that inferentially indicates the voltage across the secondary winding 258.

Another variable applied to voltage limiter 304 is the maximum voltage that can be applied to the handpiece 330. This voltage is the $V_S^{MAX}$ voltage from handpiece memory field 380.

The voltage limiter 304 also receives the measured headroom voltage, the HDRM signal, from the headroom monitor 190 as an input variable. Not shown is the circuit that provides the digitized representation of this voltage to limiter 304. A related variable applied to voltage limiter 304 is the target headroom voltage. This is a voltage level below which the headroom voltage should not drop. The target headroom voltage comes from another module run on processor 80, a target headroom calculator 312.

Figure 16:
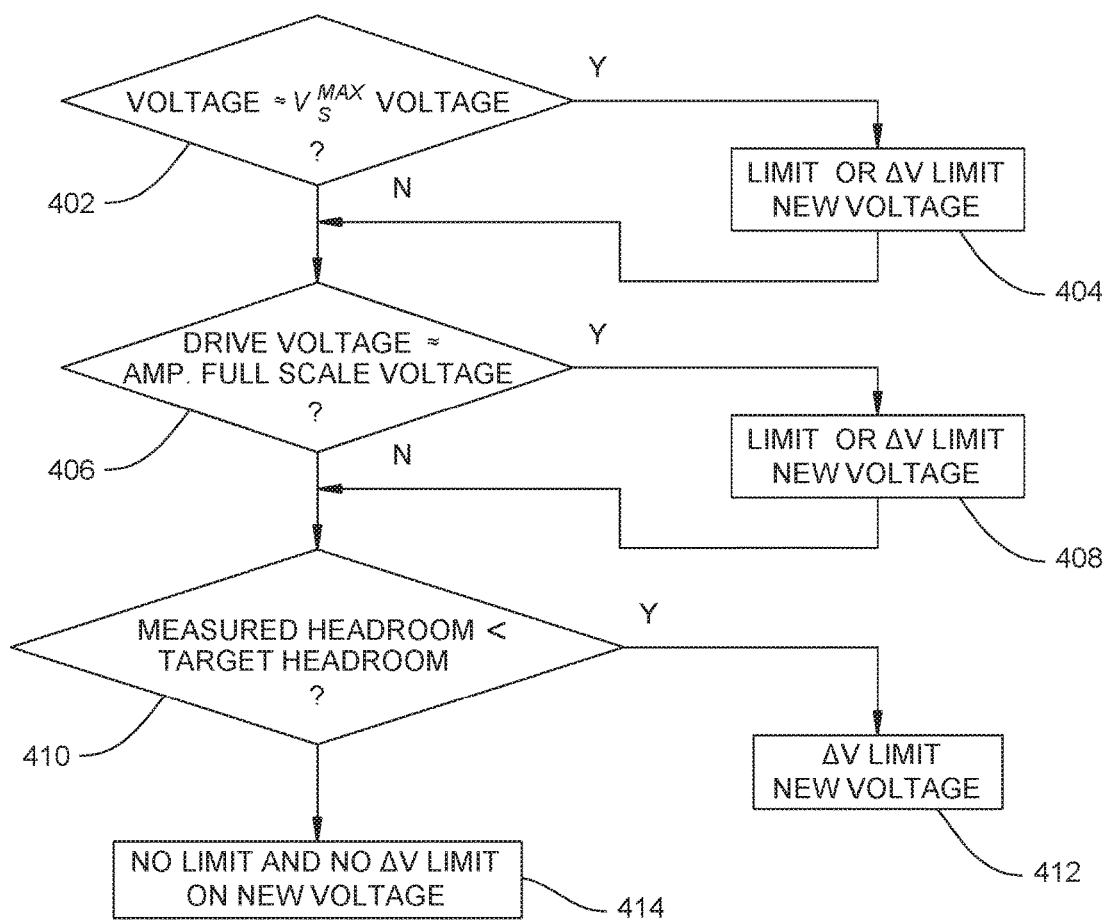
FIG. 16 is a flow chart of process steps executed by the base voltage limiter module run on the console processor.

Based on these variables and the time it takes for the limiter 304 to perform a sequence of evaluations, the voltage limiter engages in the evaluations of FIG. 16. In a first step, step 402, limiter 304 compares the voltage across the transformer secondary winding 258 to the voltage $V_S^{MAX}$, voltage limit of the drive signal.

The evaluation of step 402 may indicate that the voltage across the transformer secondary winding 258 is approaching the maximum voltage of the drive signal that can be applied to the handpiece drivers 344. If this is the result of the evaluation, in a step 404, the voltage limiter 304 asserts signals to the voltage controller 306 indicating that the control should not allow the calculated voltage for the next BASE signal to exceed a given amount. Another result of the evaluation of step 402 is that the voltage being applied to the drivers 344 is already at the maximum voltage. If this is the result of the evaluation of step 402, in step 404 the voltage limiter 304 generates a command to the voltage controller 306 indicating that the controller cannot increase the voltage of the BASE signal beyond the present level.

In a step 406, the voltage limiter 304 evaluates whether or not the voltage being allowed to develop across the transformer primary winding 252 is approaching or equal to the maximum voltage of the signal that should be allowed to develop across this winding. The level of maximum winding voltage is understood to be the lower of the maximum default maximum voltage or the maximum voltage level generated by full scale voltage calculator 298.

In step 406 it may be determined that the drive signal is near the maximum transformer voltage. If this is the result of the evaluation, in a step 408, the voltage limiter 304 outputs a command to the voltage controller that the controller should not allow the increase in the voltage of the BASE signal exceed a step amount. Another result of the evaluation of step 406 is that the voltage limiter 304 determines that the voltage across the transformer secondary winding 258 is already at the maximum permissible voltage. If this is the result of the analysis of step 406, in step 408 the voltage limiter 304 outputs a command to the voltage controller 306 that the controller cannot output a command increasing the voltage of the BASE signal beyond the present level.

In a step 410 the voltage limiter 304 evaluates whether or not the amplifier is in a state in which headroom voltage is sufficient to ensure that MOSFETs 162 and 184 will be in saturation. In step 410, compares the measured headroom voltage, the voltage based on the HDRM signal, to the target headroom voltage. In some versions of the invention, the target headroom voltage is between 2 and 20 Volts. Often the minimum target headroom voltage is between 4 and 15 Volts. If the measured headroom voltage is below the target headroom voltage, the voltage limiter 304 executes a step 412. In step 412 the voltage limiter 304 generates an instruction to the voltage controller 306 that the controller should limit the magnitude of the increase in the level of the BASE signal. More specifically, the voltage controller 306 is instructed that the controller can only increase the voltage level of the BASE signal by a set maximum amount.

In FIG. 16, step 406, is shown as being executed after step 404. Step 410 is shown as being executed after step 408. This is to represent that if necessary the voltage limiter 304 may send plural commands limited the level of voltage increase to the voltage controller 306 if any combination of the three evaluations indicate that such limitations are necessary. If any one of steps 402, 406 or 410 are executed, the voltage controller 306 acts on the received instructions and limits the level of the voltage of the drive signal contained in the instruction generated by the controller.

Often, the evaluation of step 402 indicates that the drive voltage that is to be applied does exceed the maximum voltage that should be applied to the handpiece drivers. Often in the evaluation of step 406 it is determined that the voltage that is to be developed across the console transformer 250 is below the maximum permissible voltage. Likewise, in step 410 it is often determined that the measured headroom voltage is above the target headroom voltage. When these are the results of the evaluations of steps 402, 406 and 410, as represented by step 414, the voltage limiter 304 does not assert instructions to the voltage controller 306 that result in the limiting of the level of the voltage of the BASE signal as initially calculated by the controller 306. The controller 306, when generating the instruction indicating the voltage level of the BASE signal does not attenuate the level from the level calculated in the PID calculations initially run by the controller.

Figure 15A:
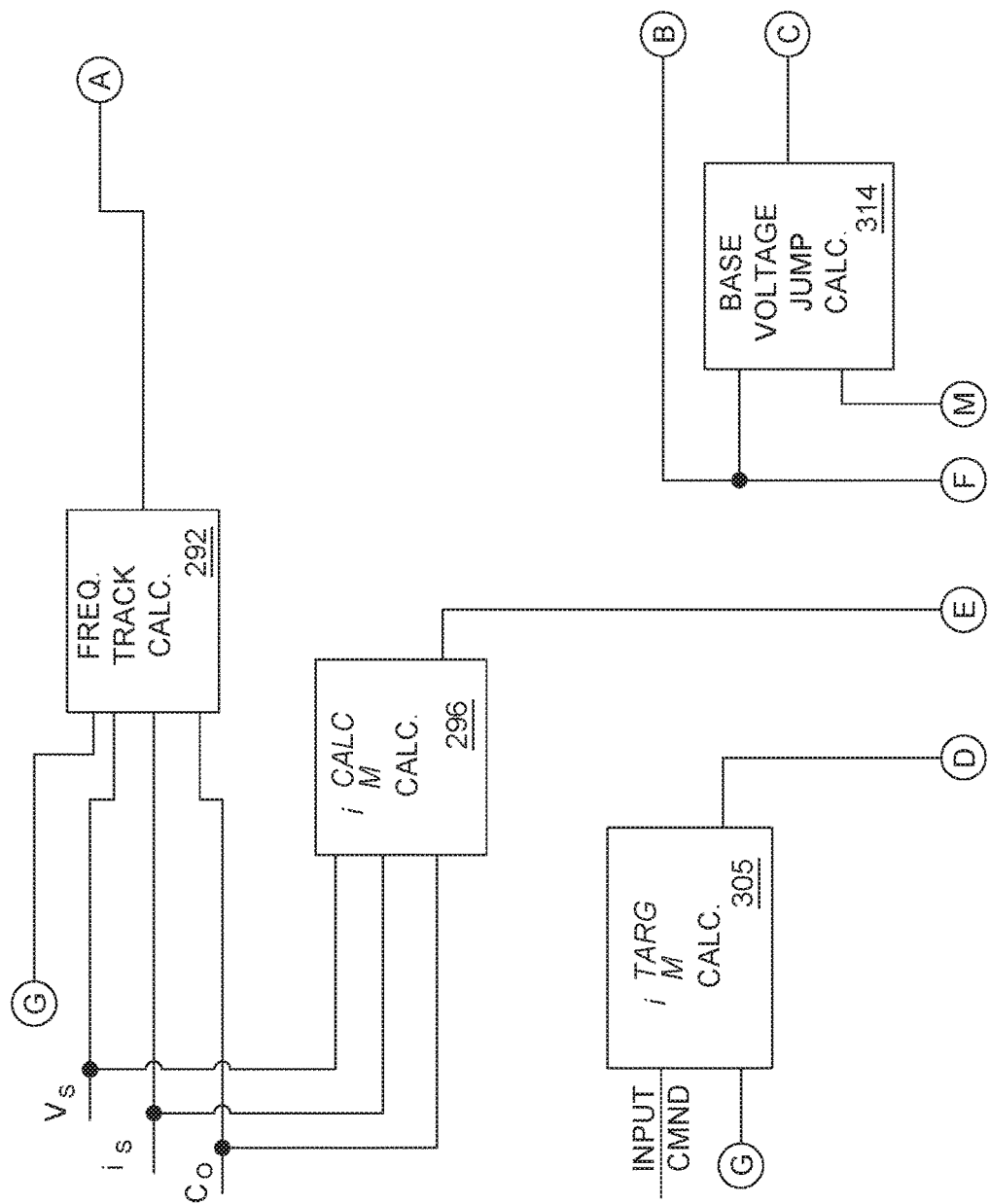
Figure 15B:
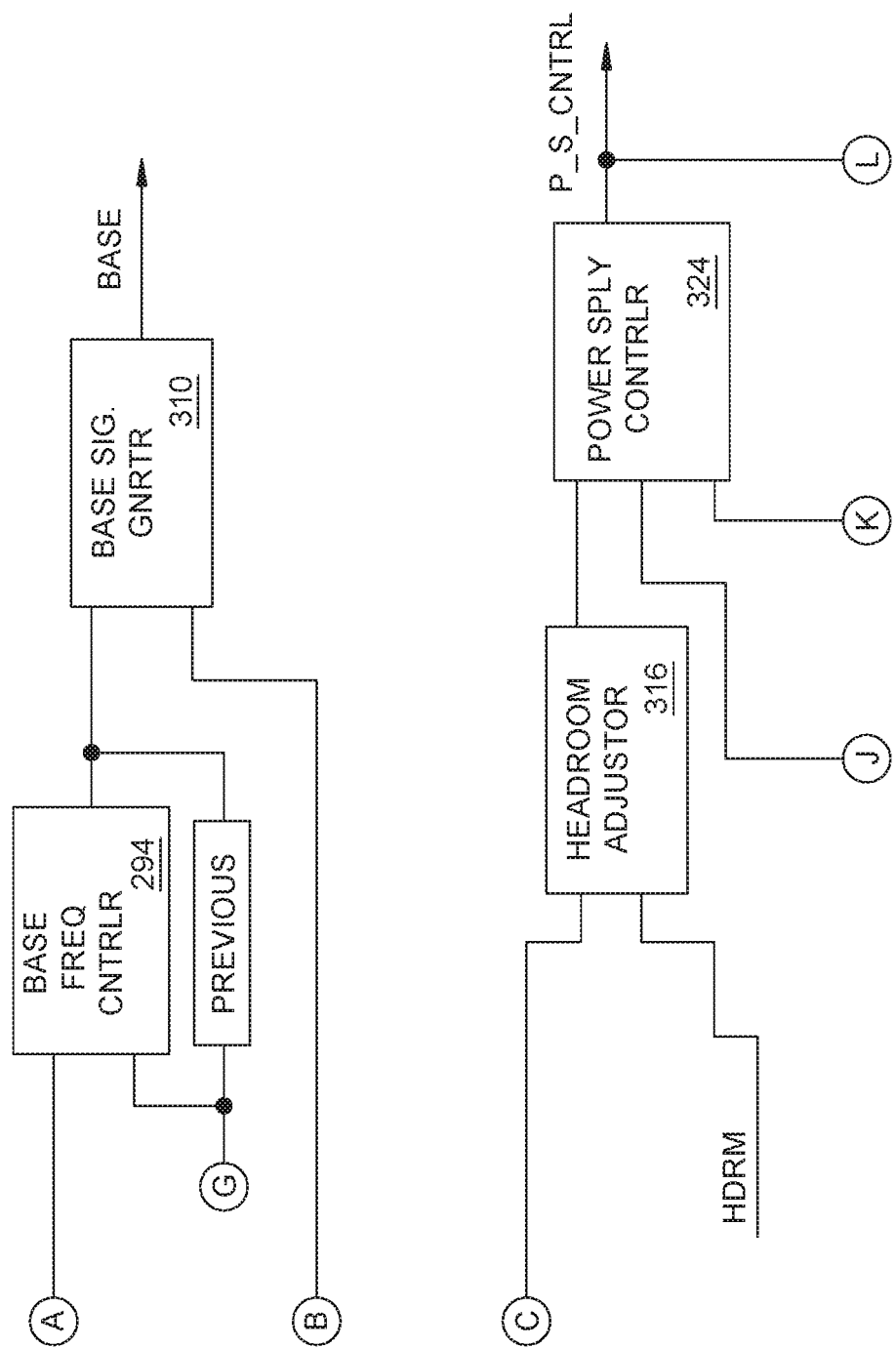
Figure 15C:
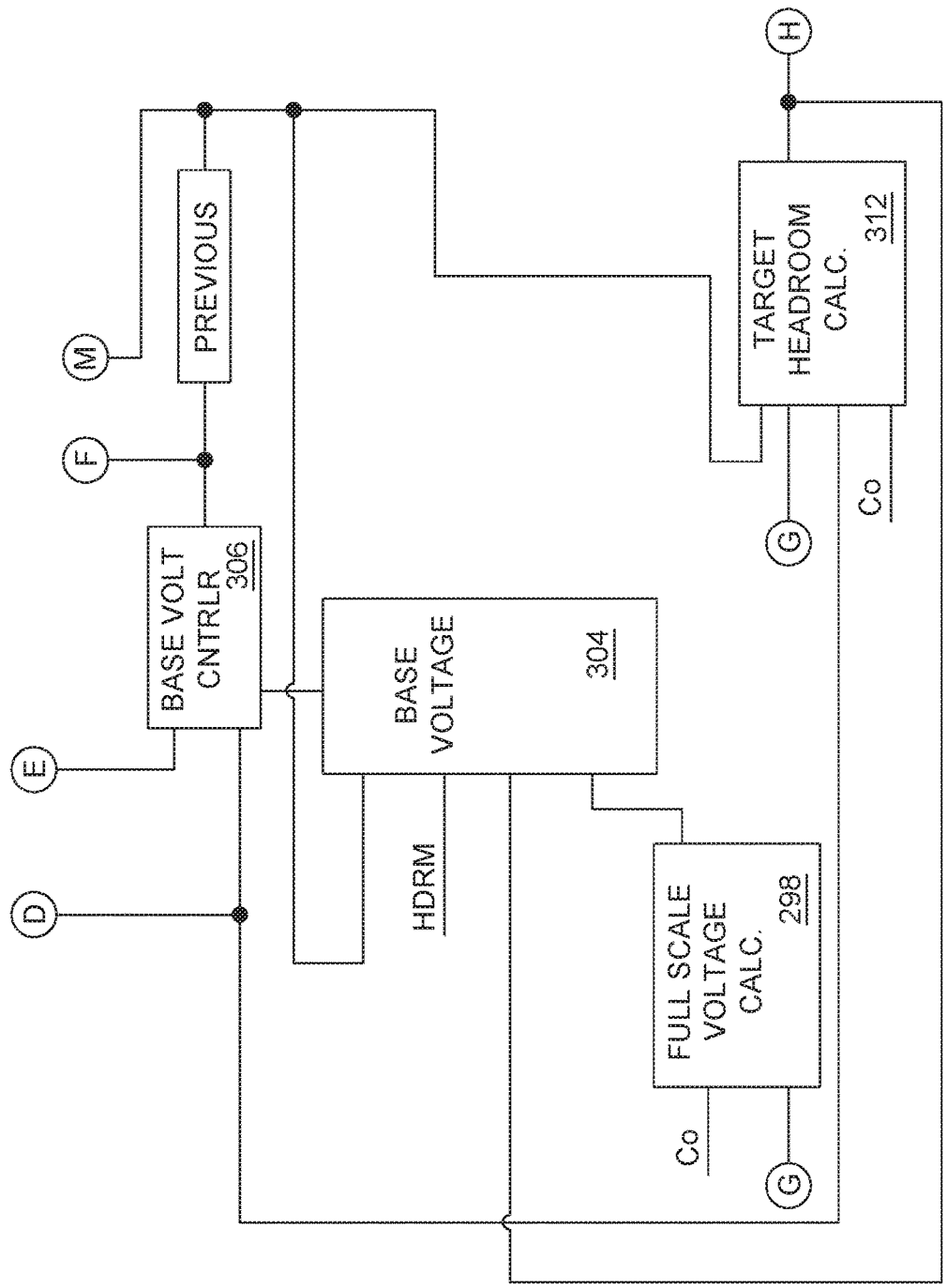

In FIGS. 15A, 15B and 15C, the instruction from the voltage controller 306 is shown applied to the base signal generator 310. As described above, the command from the frequency controller 294 is also applied to the base signal generator 310. Based on these two input commands, the base signal generator generates the appropriate BASE signal. Specifically, this is the BASE signal that is applied to amplifier 115 to causing the desired drive signal to be induced across the secondary winding 258.

As mentioned above, the control console 50 of this invention continuously adjusts the voltage applied to the center tap of transformer primary winding 252. One input variable that determines the level of this adjustment is the target headroom voltage that should be present at the drains of MOSFETs 162 and 184. This target headroom voltage, sometimes referred to as the minimum headroom voltage, could be a fixed voltage. Arbitrarily, this voltage could be 10 Volts. This headroom voltage can be considered the default headroom voltage. There are times when, owing to the characteristics of the handpiece drivers 344 and the characteristics of the drive signal applied to the drivers, this voltage is appreciably above the voltage that needs to be present to ensure that MOSFETs 162 and 184 are in saturation. Thus, when system 40 of this invention is in some operating states, the minimum headroom voltage needed to ensure the MOSFETs are in saturation may be 5 Volts or less.

The target headroom calculator 312 determines if, based on the operating state of the system 40, the target headroom voltage can be lower than the default target headroom voltage. One input into the headroom calculator 318 is handpiece driver capacitance $C_O$. Data describing the previously calculated voltage and frequency for the BASE signal are also supplied to calculator 318. An additional input into the headroom calculator 318 is the target mechanical current for the handpiece 330.

Based on the above input variables, target headroom calculator 318 determines if the target headroom voltage for the amplifier for the current operating state of the system 40 can be lower than the default target headroom voltage. When the target mechanical current is relatively low, calculator 318 can decrease the level of the target headroom voltage. When the voltage of the drive signal is relatively high, calculator 318 can also decrease the target headroom voltage. This is because, when the drive signal is relatively high for a given target mechanical current, the overall handpiece impedance is also high. This impedance may approach a maximum impedance value. This maximum impedance value is based primarily on driver capacitance. This means, during any short period of time, 0.5 seconds or less, it is unlikely that a large increase in drive signal voltage will result in the voltage present at the ends of the transformer primary winding 252 falling below what is needed to keep the MOSFETs in saturation. The headroom voltage therefore can be lowered. Driver capacitance does not directly affect the level of the target headroom voltage. However, when the drive signal frequency or capacitance is relatively high, calculator 318 increases the effect changes in the voltage of the drive signal has on the determination of the target headroom voltage.

The operating state-adjusted target headroom voltage generated by calculator 312 is the target headroom voltage provided to voltage limiter 304. In step 410, the limiter 304 compares the measured headroom voltage to this target headroom voltage.

Another module run on processor 80 to adjust the winding center tap voltage is the base voltage jump calculator 314. One input into the base voltage jump calculator 314 is the just calculated voltage level of the BASE signal generated by the base voltage controller 306. A second input into calculator 314 is the voltage level of the BASE signal generated by controller 306 in the previous calculation of this voltage. Based on these two voltages, calculator 314 determines the change in the voltage across the primary winding 252 from what is currently being applied (the voltage based on the previous cycle voltage level), to the voltage that will be presented across the winding 252 (the voltage based on the most recently calculation of voltage level). If the voltage level between cycles increasing, the value generated by calculator 314 is positive. If the voltage level between adjacent cycles decreases, the value generated by calculator 314 is negative.

The value generated by calculator 314 is applied to a headroom adjustor module 316. A second input into module 316 is the measured headroom voltage, the HDRM signal. The magnitude of the voltage change from the voltage jump calculator 314 is subtracted from the measured headroom voltage. The sum, which is output by module 316 is the adjusted measured headroom voltage. When, between two successive cycles of calculations, the voltage level of the BASE signal increases, module 316 outputs an adjusted measured headroom voltage that is less than the actual measured headroom voltage. When, between two successive cycles of calculations, the voltage level of the BASE signal decreases, the module 316 outputs an adjusted measured headroom voltage that is greater than the actual measured headroom voltage.

The adjusted headroom voltage is applied to a power supply controller 324. A second input into the power supply controller 324 is the target headroom voltage from calculator 312. Power supply controller 324 is the feedback loop controller. Controller 324 first determines the difference between the adjusted measured headroom voltage and target headroom voltage. Based on this difference and a PID algorithm, the controller 324 produces the POWER_SUPPLY_CONTROL signal. More specifically, controller 324 adjusts the POWER_SUPPLY_CONTROL signal so the voltage applied to the center tap of the transformer 250 is high enough to ensures MOSFETs 162 and 184 will be in saturation but will not be at a level that results in excessive heating of the MOSFETs.

The PID algorithm executed by controller 324 establishes the POWER_SUPPLY_CONTROL signal based on two additional variables other than the adjusted measured headroom voltage and the target headroom voltage. These variables are limit variables that define a lower boundary voltage and an upper boundary voltage for the VAMP signal based on the current voltage of the VAMP signal. These limit variables are generated by a power supply limiter 320 which is another module run on processor 80.

The input into limiter 320 is the POWER_SUPPLY_CONTROL signal previously generated by power supply controller 324. It will be understood that this voltage level of the POWER_SUPPLY_CONTROL signal is proportional to the center tap voltage. Limiter 320 therefore uses the magnitude of POWER_SUPPLY_CONTROL signal as a proportional substitute for the center tap voltage being applied to the transformer 250.

Figure 17:
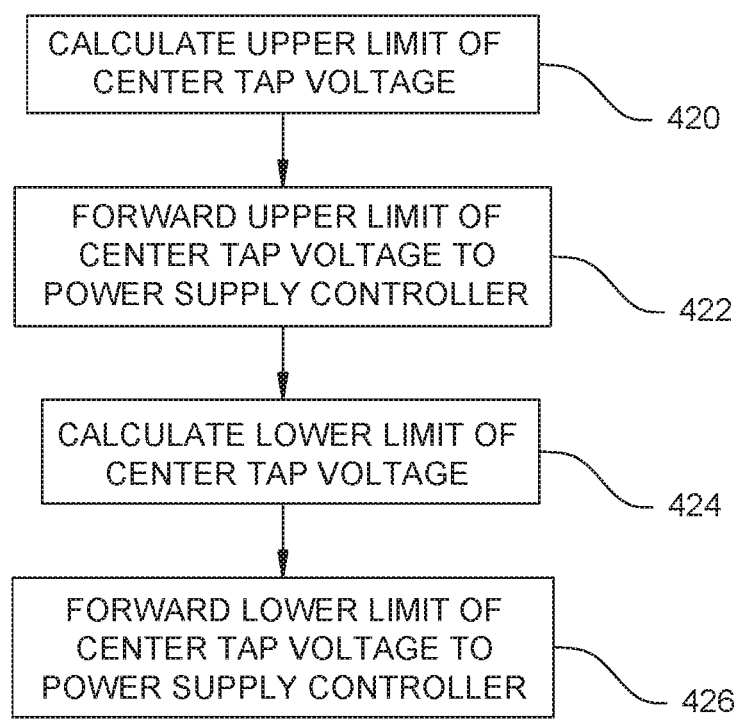
FIG. 17 is a flow chart of process steps executed by the power supply voltage limiter module run on the console processor.

Based on this signal representative of the present center tap voltage, as represented by FIG. 17, the limiter generates two instructions to the controller 324. Specifically, in a step 420, limiter calculates a maximum level for the voltage that should next be generated by the center tap. It is necessary to generate this maximum voltage because there is a limit to the rate the adjustable boost converter 88 can ramp up the voltage applied to the center tap. By limiting the rate of increase in the POWER_SUPPLY_CONTROL signal, processor 80 substantially eliminates the likelihood that the power supply amplifier will receive signals that would attempt to force the boost converter 88 to operate beyond its design specifications.

In many versions of the invention, the maximum level of the change for the center tap voltage is a fixed scalar value throughout the range of center tap voltages. In these versions of the invention, in step 420, this POWER_SUPPLY_CONTROL voltage equivalent of this voltage is added to the value of the previous POWER_SUPPLY_CONTROL voltage received from controller 324. Step 422 represents limiter 320 sending an instruction with this upper limit for the POWER_SUPPLY_CONTROL signal to controller 324.

In a step 424 the power supply limiter 320 generates a minimum level for the center tap voltage. The reason it is desirable to limit the rate at which the center tap voltage is allowed to drop is appreciated by understanding how a handpiece of this invention is used. During the course of a procedure, the handpiece is moved so the tip 360 is repeatedly moved against and retracted away from the tissue on which the procedure is being performed. When the tip 360 is applied to the tissue, the tip is under a relatively large mechanical load. When the tip 360 is retracted away from the tissue, the mechanical load to which the tip is exposed rapidly drops. This results in a like drop in the equivalent of current $i_M$ through the mechanical components of the handpiece. Controller 80 is configured to hold this equivalent of current constant. Accordingly, when handpiece is moved away from the tissue, the controller reduces the voltage of the BASE signal to reduce the voltage $V_S$ of the drive signal.

This drop in drive signal voltage means it would be possible to appreciably reduce the voltage that power supply 84 applies to the center tap of the transformer 250. Again, it is desirable to keep this voltage as low as possible to minimize heat loss through MOSFETs 162 and 184.

However, during the procedure, the handpiece tip 360 can be held against tissue for a time period of 2 seconds or less, retracted away from the tissue for a time period of 2 seconds or less and then again reapplied to the tissue. During the short time period the tip is retracted away from the tissue, the power supply 84 could be instructed to, significantly reduce the voltage applied to the center tap again. If this event occurs, when the tip head 364 is again applied to the tissue, the system may be in a state in which the center tap voltage is not at a level sufficient to maintain the voltages present across MOSFETs 162 and 184 above the target headroom voltage. If the console enters this state, as discussed above, base voltage limiter 304 and base voltage controller 306 cooperate to limit the rate of increase in the voltage, drive signal voltage. This would mean that when the tip head 364 is again applied to the tissue, that could be a relatively long lead time before the drive signal voltage ramps to a level that would result in the tip vibrations desired by the practitioner.

To reduce the incidence of the practitioner having to wait for the tip vibrations to ramp up, power supply limiter 320 limits the rate at which power supply controller 324 is able to lower the center tap voltage. Specifically, the power supply limiter in a step 424 calculates a lower limit of the next POWER_SUPPLY_CONTROL signal that the controller 324 can produce. In some versions of the invention, step 424 is performed by subtracting a fixed value to the value of previous POWER_SUPPLY_CONTROL signal the controller forwarded to the limiter 320.

In many versions of the invention, this fixed value of maximum permitted decrease in level of the POWER_SUPPLY_CONTROL signal is less than the fixed value of the maximum permitted increase in the level of the POWER_SUPPLY_CONTROL signal. This is because, the rapid response to the increase in load applied to the tip is more beneficial than limiting the loss of heat through the MOSFETs 162 and 184.

In a step 426 the power supply limiter 304 sends an instruction to the power supply controller 306 indicating the minimum level of the POWER_SUPPLY_CONTROL signal the controller is allowed to output.

The voltage limits generated by the power supply limiter 304 function as the output range limit variables of the PID algorithm executed by the power supply controller 320. This ensures that the calculated POWER_SUPPLY_CONTROL signal subsequently applied to the boost circuit will not result in the output of a VAMP signal that is outside of the range of voltages for this signal given the present state of this signal.

The power supply controller 324 also ensures that the output POWER_SUPPLY_CONTROL signal does not cause a VAMP signal to appear at the center tap of the primary winding 252 that is outside of the operating range of the console 50. Specifically, the POWER_SUPPLY_CONTROL signal is not allowed to drop below a level that would result in the center tap voltage falling before a minimum voltage level. Often this minimum voltage level is between 10 and 50 Volts. Similarly, controller 320, if necessary, limits the POWER_SUPPLY_CONTROL signal to prevent the power supply from applying a voltage to the center tap that is above a design limit. Typically, this voltage is between 100 and 500 Volts. More often the limit of this voltage is between 200 and 400 Volts. In one version of this invention, this voltage is 250 volts.

System 40 of this invention is configured for use by attaching a tip 360 to the handpiece 330. Handpiece cable 326 is attached to console 50. When the console 50 is first actuated, processor 80, through memory reader 78, reads the data in handpiece memory 338. The reading of the data in the handpiece memory 338 into the processor 80 essentially completes the process of readying the system 40 for use.

The practitioner sets the amplitude of tip head 364 vibrations by setting the position of slide switch 56 or otherwise entering the appropriate command through display 82.

The practitioner actuates the handpiece by depressing the foot pedal 54 or equivalent control member. In response to the processor 80 receiving the command to so actuate handpiece 330, vibrate the tip 360, the console generates instructions that cause the power supply 84 to output a voltage to the center tap of the transformer primary winding 252. For the purposes of understanding the present invention, these instructions include the outputting of an initial POWER_SUPPLY_CONTROL signal to the boost converter 88. Processor 80 also outputs instructions that cause an AC signal to appear across the transformer primary winding 252. For the purposes of understanding the present invention, these instructions include the outputting of the BASE signal.

In response to an AC signal appearing across the transformer primary winding 252, a signal is introduced across the secondary winding 258. The signal across the secondary winding is the drive signal. The drive signal is output from the console 50 over cable 326 to the handpiece drivers 338. The application of the drive signal to the drivers 338 results in the vibration of the drivers. The vibrations of the drivers are transferred through the horn 356 and tip stem 362 to the head 364 to result in the desired vibration of the head.

During the actuation of the handpiece, the POWER_SUPPLY_CONTROL signal and a signal proportional to the VAMP signal are applied to the DC/DC controller 90. Based on the states of these signals, DC/DC controller 90 selectively gates the MOSFETs 112. The MOSFETs 112 are gated to cause the controller 90 to output a VAMP signal to the transformer center tap that is at the voltage specified by the POWER_SUPPLY_CONTROL signal.

While the handpiece 330 is actuated, signals proportional to the signals present at the opposed ends of the transformer primary winding 252 are supplied to the opposed inputs of differential amplifier 118, more precisely, amplifier 240. These signals are understood to be out of phase with each other. Amplifier 240 and associated components thus output an attenuated version of the difference between the signals to the summing amplifier 122.

The output signal from amplifier 240 and the BASE signal are combined prior to being applied to the inverting input of summing amplifier 122. Ideally, these two signals are 180° out of phase. In actuality, the signals are not out of phase. Summing amplifier 122 therefore produces an AC signal based on the difference between the two input signals. In many versions of the invention, this signal is amplified version of the difference between the two signals. This signal is the feedback adjusted BASE signal. Rectifier and splitter 138 splits the feedback adjusted BASE signal into its the positive and negative components.

The negative component of the feedback adjusted BASE signal is the input signal into the inverting voltage controlled current source 156. Based on the voltage of this signal, current source 156 selectively turns MOSFET 162 on and off. The positive component of the feedback adjusted BASE signal is the input signal into noninverting voltage controlled current source 174. Based on the voltage of this signal, current source 174 selectively turns MOSFET 184 on and off. Owing to the application of the bias voltages to current sources 156 and 174, there is never a time when MOSFETs 162 and 184 are ever turned fully off. This means that when the primary winding voltage transitions between the positive and negative states, there is essentially no break or discontinuity in the rate of change of this potential. By extension, this ensures that the drive signal that is induced across the transformer secondary winding 258 is does not have any unusual inflections. In other words, the drive signal is essentially sinusoidal in shape. The application of this sinusoidal drive signal to the handpiece drivers 344 ensures that the drivers contract and expand at even, regular rates.

Further, console 50 is constructed so that control of the potential allowed to develop across the transformer primary winding 252 is based on two inputs. The first input is the BASE signal, the signal that sets the target for the potential that should develop across winding 252. The second input is the feedback signal, the actual potential across winding 252. This feature of the invention ensures that, with a reasonable degree of accuracy, a change in the voltage of the BASE signal results in a substantially linear corresponding change in the voltage across the primary winding 252. This, in turn, results in the signal that is induced across the secondary winding 258 and applied to the handpiece as the drive signal as having relatively ideal characteristics. Here, relatively ideal characteristics are the characteristics that cause the drive signal to, when applied to the drivers 344, result in the pattern of tip head 364 vibrations desired by the surgeon to perform the procedure.

Inductor 187 reduces the extent to which the voltage across and the current flows through each of MOSFETs 162 and 184 are out of phase. During periods of relatively high voltage across or current flow through each MOSFET 162 or 194, the MOSFET generates an appreciable amount of heat in comparison to when there is a lower voltage across or lower current through the MOSFET. By regulating these voltages and currents there are time periods when both the voltage across and current through the MOSFET 162 or 184 are relatively low. This serves to, during these time periods, reduce the amount of heat generated by the MOSFET 162 or 184. The reduction in this MOSFET-generated heat reduces the overall amount of heat generated by the control console of this invention.

The frequency tracking calculator 292 and base frequency controller 294 monitor and, when necessary, adjust the frequency of the BASE signal output by processor 80. This ensures that, when the mechanical load to which the tip 360 is exposed changes, the frequency of the drive signal maintains the appropriate relationship relative to handpiece resonant frequency in order to facilitate the desired vibrations of the tip head 364.

The base voltage controller 306, when necessary, adjusts the voltage of the BASE signal. This adjustment is performed to also ensure that when the load of the tip head 364 changes, the tip head 364 continues to have vibrations of the amplitude desired by the practitioner in order to accomplish the procedure.

Base voltage limiter 304 essentially eliminates the likelihood that an increase in the voltage of the BASE signal could result in a voltage appearing across the transformer primary winding that takes MOSFETs 162 and 184 out of saturation. This results in a like substantial elimination of the possibility that when it is necessary to rapidly increase the drive signal, owing to the MOSFETs being out of saturation, the drive signals will be clipped. If this clipping of the drive signal is allowed to occur, the drivers and tip could transition from undergoing regular expansions and contracts to a movement that is less periodic. This clipping can also induce undesirable vibration modes in the tip.

Other modules on the processor 80 regulate the voltage of the signal applied to the center tap of the transformer primary winding 252 The voltage jump calculator 314 and headroom adjustor 316 collectively provide an adjusted value of the headroom voltage that is a look forward measurement of this voltage. By look forward measurement, it is understood to be the value of this measurement if the is no change in the voltage applied to the transformer center tap and there is a change in the voltage difference across the ends of the primary winding 252. This gives the power supply controller 324 the ability to adjust the center tap voltage in anticipation of the change in the voltage across the transformer winding 252.

When system 40 is in a state in which the voltage of the drive signal increases, this feature causes the center tap voltage to start to ramp up when there indication that the drive voltage will so increase. This reduces the likelihood that owing to a rapid increase in drive signal voltage, the evaluation of step 390 will test positive. Again, when in step 390 it appears that the measured headroom voltage falls below the target headroom voltage the processor will slow the rate at which the drive voltage is ramped up.

When system 40 is in a state in which the voltage of the drive signal decreases, this feature of the invention facilitates the lower of the center tap voltage. This reduces the voltage drop across the MOSFETs 162 and 184 so as to reduce the heat loss through the MOSFETs.

A further feature of this invention, is that when the voltage of the drive signal is decreased, the power supply limiter 320 only allows the transformer center tap voltage to decrease at a relatively slow rate. Here this rate of voltage decrease is understood to be relatively slow in comparison the power supply voltage limiter 304 allows the transformer center tap voltage to increase. This feature of the invention system 40 is of use when during a procedure the tip head 260 is moved back and forth, towards and away from, the tissue being subjected to the removal procedure. During the phases of this use of the handpiece 330 when the tip is moved towards the tissue, this feature of the invention ensures that owing to the center tap voltage not appreciably falling, there is sufficient headroom voltage to allow the rapid ramping up of the voltage of the drive signal. The allowing of this rapid rise in drive signal voltage means reduces the loss of energy that occurs when the tip 364 is initial pressed against the tissue.

When system 40 of this invention is in certain operating states, the target headroom voltage calculator 312 lowers the target headroom voltage from the default level for this voltage. This allows the console to, when system 40 is in these states reduce the center tap voltage to that at which must be maintained when the target headroom voltage is at the default level. This feature of the invention further reduces the level of voltage that has to be maintained across MOSFETs 162 and 184 and the undesirable effects of maintain this voltage at a high level.

Further the linear amplifier 115 of this invention is able to amplify BASE signals with little distortion over a relatively wide frequencies. In many versions of the invention, the console is able to output drive signals between 15 kHz and 45 kHz. In still more preferred versions of the invention, the console is able to output drive signals with no or acceptable levels of distortion between 10 kHz and 100 kHz. Thus, the system of this invention is well suited to drive ultrasonic handpieces to which drive signals have multiple components are applied. More specifically, the console of this invention can be used to produce a drive signal wherein the individual components of the signal differ in frequency by 2,000 Hz or more.

The above describe is directed to a specific embodiments of the system 40 of this invention.

Alternative versions of this invention are possible. For example, there is no requirement that each of the above described features be included in each version of the system of this invention. Thus, it is within the scope of this invention, to provide a console with a Class A amplifier, a Class B amplifier, a Class AB amplifier, or variation of these amplifiers and a power supply that provides a fixed voltage to the center tap of the transformer primary winding. The system of this invention can thus include one or two Class A amplifiers or one or two Class B amplifiers.

In versions of the invention wherein the console monitors the headroom voltage and adjusts the center tap voltage based on the headroom voltage, not all features of the disclosed system may be present. Thus, in an alternative version of the system the monitored headroom voltage may not be adjusted based on a look forward change in winding voltage prior to being compared to the target headroom voltage. In some versions of the invention, the target headroom voltage may be a fixed value.

Similarly, some versions of the console 50 may be constructed so that there is no need to provide a module like the full scale voltage calculator 298 that lowers the maximum voltage the processor 80 allows to appear across the primary winding 252.

The structure of the features of the invention may likewise change from what is described. Bipolar transistors can substitute for one or more of the MOSFETs. However, given that voltages in excess of 150 volts peak may be present at the ends of transformer primary winding 252, it is believed MOSFETs are a preferred form of active resistors for selectively connecting the winding to ground or effectively, an open circuit. The amplifiers, the rectifier and splitter, the current sources and the power supply that supplies the VAMP signal to the transformer center tap may have structures different from what has been described In the described version of the invention, the headroom monitor 190 is configured to monitor the voltages present between the drains of each of MOSFETs 162 and 184 and ground. In an alternative version of the invention, the headroom monitor may be constructed to monitor the drain to source voltages across the MOSFETs 162 and 184. In versions of the invention wherein the bipolar transistors function as the active resistors, this type of headroom monitor would monitor the collector emitter voltage across the transistors.

Figure 18:
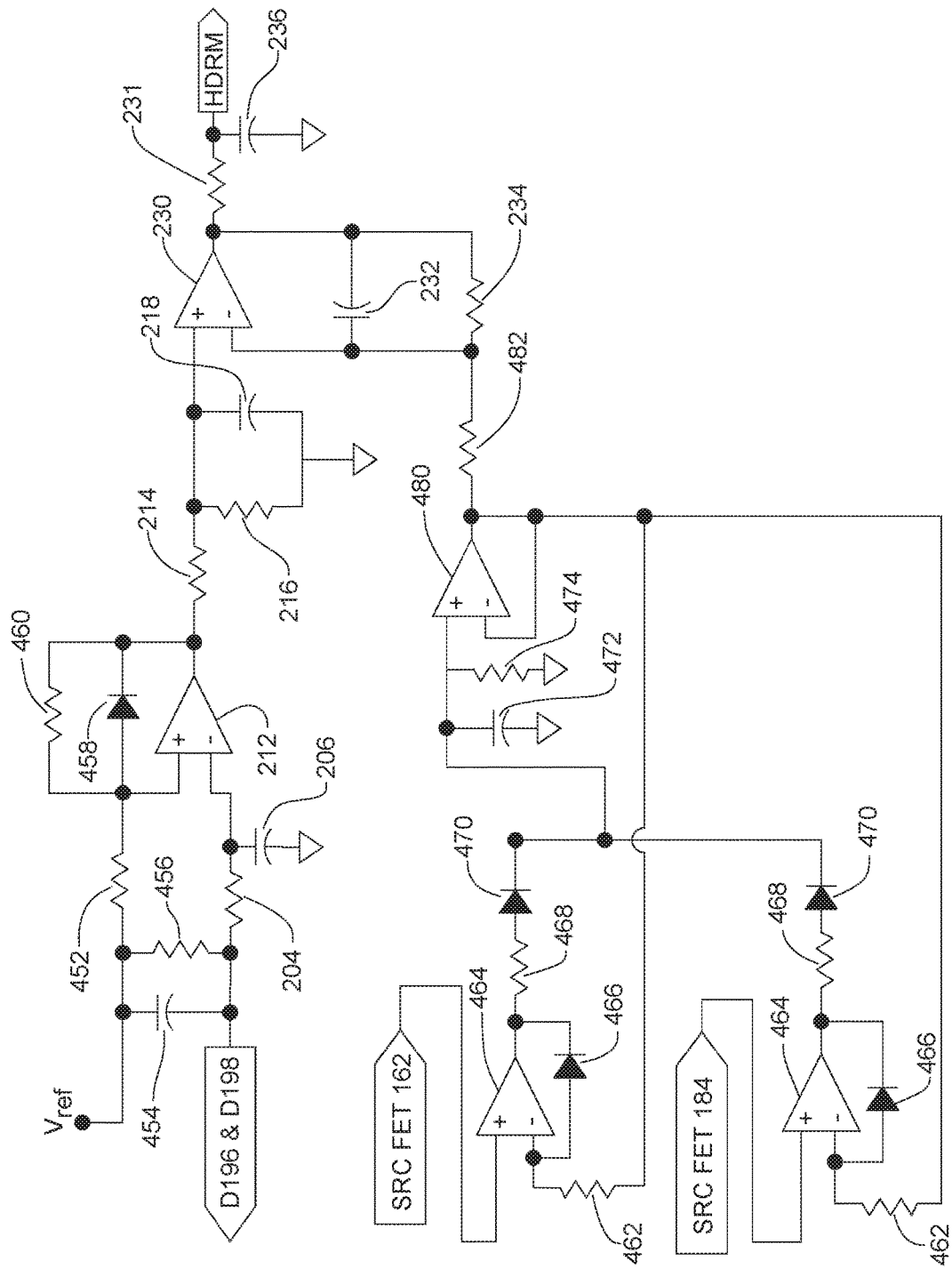
FIG. 18 is a schematic drawing of an alternative circuit of this invention for producing a signal representative across the transistors that form the active resistors of the linear amplifier.

One such headroom voltage monitoring circuit is now described by reference to FIG. 18. This circuit substitutes for the circuit capable of monitoring the headroom voltage described with reference to FIG. 6A. Some of the component of the circuit of FIG. 6A are included in the circuit of FIG. 18. To avoid redundancy in this document, the components previously described are now only minimally described again. the input. In the circuit of FIG. 18, like the circuit of FIG. 6A, the anodes of diodes 196 and 198 are connected to the noninverting input of amplifier 212. The anodes of diodes 196 and 198 are connected to amplifier 212 through resistor 204. A reference voltage $V_{ref}$ is applied to the inverting input of amplifier 212 through a resistor 452. In some versions of this invention voltage $V_{ref}$ is a constant voltage between 15 and 30 VDC. Not illustrated and not part of the invention is the circuit internal to console 50 that generates voltage $V_{ref}$. A capacitor 454 is tied between the rail to on which the $V_{ref}$ is present and the junction between the diodes 196 and 198 and resistor 204. A resistor 456 is connected in parallel across capacitor 454.

A diode 458 and a resistor 460 are connected parallel between the inverting input of amplifier 212 and the output of the amplifier. More specifically, the anode of diode 458 is connected to the inverting input of amplifier 212; the cathode is connected to the junction of the amplifier and resistor 214.

The circuit of FIG. 18 also receives as inputs the voltages present at the sources of MOSFETs 162 and 184. Each of these voltages is applied to a unity gain amplifier circuit that functions as a rectifier. The amplifier circuit to which the signal present at the source of MOSFET 162 is applied includes an amplifier 464. The signal present at the source of the MOSFET 162 is applied to the noninverting input of the amplifier 464. Not identified are the resistor through which the voltage is applied to the noninverting input of amplifier 464 or the capacitor tied between this input and ground. The anode of a diode 466 is connected to the inverting input into amplifier 464. The cathode of diode 466 is tied to the output of the amplifier 464. The signal present at the Output of amplifier 464 is applied through a resistor 468 to the anode of a diode 470.

The source of MOSFET 184 is tied to the same type of rectifier to which the source of MOSFET 162 is applied.

The signals present at the cathodes of diodes 470 are both applied to the noninverting input of an amplifier 480. A capacitor 472 is tied between the junctions of the diodes 470 and the input into amplifier 480. A resistor 474 is connected in parallel across capacitor 472. The signal present at the output of amplifier 480 is applied back to the inverting input of the amplifier. The signal present at the output of amplifier 480 is through separate resistors 462 applied to the inverting input of each of the amplifiers 464.

The signal present at the output of amplifier 480 is, through a resistor 482, applied to the inverting input of amplifier 230. Thus, the input into the noninverting input of amplifier 230 is the lower of the two voltages present at the drains of MOSFETs 162 and 184. The input into the inverting input of amplifier 230 is the higher of the two peak voltages present at the sources of the MOSFETs 162 and 184. The output of amplifier 230 is the difference between the minimum one of these drain voltages and the higher of the one of these source voltages. This is the signal that is output by the circuit of FIG. 18, at the junction of resistor 231 and capacitor 236 and the HEADROOM voltage.

In some versions of the invention, the signal gain of the individual sub-circuits of the amplifier may be lower or higher than what has been described.

Alternative assemblies for monitoring the headroom voltages are also possible. In the described system, the analog circuit produces the HDRM signal. In other versions of the invention, the analog circuit may include a FET that substitutes for the resistor disposed across capacitor 192. Each control loop cycle the capacitor is turned on once to discharge the capacitor 192. This would increase the response rate of the headroom monitoring circuit to changes in the voltages measured at the transistors. Other means may be employed to provide the reference voltage applied to the inverting input of amplifier 230. Thus, the voltage could be provided from a digital to analog converter. This is useful in versions of the invention in which it may be desirable to change the potential of the reference voltage. In other versions of this invention, drains of collectors of the switching transistors are digitized and applied to the processor 80. A module run on the processor evaluates these voltage measurements and based on the evaluation produces the HDRM signal.

Similarly, the control processes, the control modules, run on the console processor 80 may operate differently from what has been described.

This invention is not limited to ultrasonic tool systems wherein equations based on Equations (1) to (3) are used to determine the voltage and frequency of the drive signal. Other versions of the invention, may not rely of comparisons based on any one of measured, measured voltage, drive signal frequency, the equivalent of mechanical current to determine the voltage and frequency of the drive signal.

For example, in some versions of the invention the default target headroom voltage may be the lowest possible target headroom voltage. In these versions of the invention, based on the operating state of the system, the headroom voltage calculator selectively increases the headroom voltage to a level above the default value. This construction of the invention can further reduce the extent to which the voltage drop across the MOSFETs 162 and 184 is in excess of what is needed to hold the transistors 162 and 184 in saturation.

In some versions of the invention, the headroom adjustor simply consists of a module that adds a fixed value to the measured headroom. It is acknowledged that this version of the system may result in the center tap voltage sometime being in excess of what is needed to hold the MOSFETs 162 and 184. A benefit of this version of the invention, is that it reduces the time required to generate the value of the adjusted measured headroom.

In some versions of the invention, power supply limiter 320 outputs voltage limits for the next adjustment of the POWER_SUPPLY_CONTROL signal by multiplying the current voltage of the VAMP signal by a fixed coefficient. In still other versions of the invention one or both of the power supply limiter 320 or power supply controller 324 is or are configured to prevent the controller 324 from, immediately after the voltage of the drive signal is to be lowered, lowering the voltage applied to the transformer center tap. For example, in some versions of this invention, console 50 is constructed to prevent the voltage of this signal from being lowered until a period of 1 to 5 seconds has passed from when the console starts to lower the drive signal. A benefit of this arrangement is that during the phase of a procedure in which the tip head 364 is reapplied to the bone, the center tap voltage will clearly be at a voltage that will allow the processor to rapidly increase the voltage of the drive signal.

In some versions of the invention, the power supply controller 324 many not use the voltage limits output by the power supply limiter 320 in a primary PID control algorithm to calculate the next value of the POWER_SUPPLY_CONTROL signal. Instead, in these versions of the invention, the power supply controller 324 compares an initially calculated POWER_SUPPLY_CONTROL signal to the voltage limits. If this initial POWER_SUPPLY_CONTROL signal is within the voltage limits, initially calculated POWER_SUPPLY_CONTROL signal is the POWER_SUPPLY_CONTROL output to the boost converter 88. If the initially calculated POWER_SUPPLY_CONTROL signal is outside of the voltage limit, one of two possible events may occur. In some versions of the invention, the closest voltage limit is output as the POWER_SUPPLY_CONTROL signal.

In other versions of the invention, the power supply controller 324 reexcutes the PID control algorithm. In this execution of the PID control algorithm, the voltage limit is employed as the target headroom voltage. A benefit of this version of the invention is that each individual execution of the PID algorithm does not include a step to limit the POWER_SUPPLY_CONTROL signal. It should however be appreciated that should it be necessary to voltage limit the POWER_SUPPLY_CONTROL signal, two executions of the PID algorithm are performed. The first execution produces the initial POWER_SUPPLY_CONTROL signal, the signal indicating that the center tap voltage will fall outside of the limits defined by the power supply voltage limiter 320. The second execution of the algorithm produces the POWER_SUPPLY_CONTROL signal that will result in the boost voltage being within the defined voltage limits.

It should thus be appreciated that all the disclosed software modules run on the processor 80 may not be present or may be present in different form. For example, there may be a construction of the invention in which loss of heat through the transistors functioning as the active resistors, MOSFETs 162 and 184, in the disclosed version of the invention, is not a significant concern. In these versions of the invention as well as other versions of the invention the center tap voltage may be kept constant. Alternatively, while the voltage applied to the center tap voltage may be varied, the voltage may be set to have a relatively high minimum voltage level, a minimum voltage of 25 Volts or possible a minimum voltage of 50 Volts or more. In these versions of the invention, the voltages present at the drains or collectors of the transistors would always be in saturation. This would eliminate the need for the voltage limiter 304 to limit increases in the voltage level of the BASE signal to ensure that the amplifier is in this state. This may make it possible to not require that presence of the above described power supply limiter.

In versions of the invention where the center tap voltage is constant, the power supply that produces this voltage may not be a variable power supply. This would eliminate the need to provide software for setting the DC voltage of the signal produced by this power supply.

Here for the purposes of this invention, it is understood that the DC voltage applied to the center tap of the transformer primary winding 252 is a voltage above ground. This voltage may even be considered constant if for some design consideration not relevant to the current invention, the voltage level varies at a constant frequency.

In some versions of the invention wherein the center tap voltage is regulated to ensure the proper headroom voltage, it may be possible to not include the circuit that produces a measure of the headroom voltage. In these versions of the invention, virtual value of headroom voltage is calculated based as a function of drive signal voltage and/or drive signal current.

In some versions of the invention, voltages across resistors attached to the transformer secondary winding provide the signals upon which at least one of drive signal voltage or drive signal current is based.

The invention is also not limited to amplifiers wherein a boost converter functions as the variable DC voltage power supply. One alternative power supply is a buck converter.

There may be alternative control consoles that do not include all the inventive features of the described console 50. Thus, some consoles of this invention may include the linear amplifier of this invention and not include either of the described headroom voltage measuring circuits. Similarly, there may be versions of the invention wherein it may be desirable to employ one of the headroom voltage measuring circuits of this invention without the described linear amplifier.

It would be possible to provide an amplifier of this invention wherein the amplifier, instead of being a voltage controlled voltage source, is a voltage controlled current source. In these versions of the invention, it is typically not necessary to provide the feedback loop for regulating the voltage of the signal applied to the transformer primary winding.

Likewise, it should be understood that the control console 50 of this invention may be used to provide AC drive signals to surgical tools other than handpieces that include power generating units other than ultrasonic drivers. For example, the control console may be used to provide an AC drive signal where the power generating unit is a sub-assembly that, in response to the application of the drive signal, emits light (photonic energy) or some form of mechanical energy other than ultrasonic energy. Alternatively the power generating unit may be an electrode that applies the drive signal, which is a form of RF energy, to the tissue to which the electrode is applied. In this type of procedure, the electrical energy is applied to the tissue so as to turn the electrical energy into heat. The application of this heat causes a desirable therapeutic effect on the tissue. Typically, this therapeutic effect is the ablation of the tissue.

Further, the transformer and associated linear amplifier of this invention may have applications for generating a drive signal that is used to power a device used to perform a task other than a task associated with medicine or surgery.

Accordingly, it is an object of the appended claims to cover all such variations and modifications that come within the true spirit and scope of this invention.

What is claimed is:

1. An AC signal generator for an ultrasonic handpiece including a driver and a tip coupled to the at least one driver that vibrates upon actuation of the driver, the AC signal generator comprising:
   a transformer including a primary winding with opposed ends and a center tap to which a DC voltage is applied; and a secondary winding across which an AC drive signal is induced for actuating the driver of the handpiece; and
   a linear amplifier including:
      first and second transistors that function as first and second active resistors respectively that are each connected to a separate end of the opposed ends of said primary winding of said transformer and ground, wherein said linear transformer is configured to set the resistances of said first and second active resistors implemented by the first and second transistors to set the voltage at each opposed end of the primary winding between a ground state voltage and an open state voltage that so as to causes an AC voltage to develop across the primary winding that causes the AC drive signal to develop across said secondary winding;
      a differential amplifier to which the voltages present at the opposed ends of the transformer primary winding are applied and that produces as a feedback signal a signal based on the differences between the voltages present at the opposed ends of the transformer primary winding for causing, responsive to receipt of an external control signal, a substantially linear response of the AC voltage developed across the primary winding that causes desired vibrations of the tip of the handpiece upon actuation of the driver by the AC drive signal developed across the secondary winding according to the external control signal; and
      a control circuit that receives the feedback signal and the external control signal and that, based on the feedback signal and the external control signal, sets the resistances of said first and second active resistors implemented by said first and second transistors for generating the substantially linear response.

2. The AC signal generator of claim 1, wherein said control circuit of said linear amplifier is configured to combine the feedback signal from said differential amplifier with the external control signal to produce a combined signal that regulates the resistances of said first and second active resistors implemented by said first and second transistors.

3. The AC signal generator of claim 2, wherein said linear amplifier control circuit includes a rectifier and splitter to which the combined signal is applied, said rectifier and splitter being configured to split the combined signal into positive and negative components wherein the negative component of the combined signal is used to set the resistance of said first active resistor implemented by said first transistor and the positive component of the combined signal is used to set the resistance of said second active resistor implemented by said second transistor.

4. The AC signal generator of claim 1, wherein said control circuit of said linear amplifier includes a first voltage controlled current source and a second voltage controlled current source that, based on the feedback signal from said differential amplifier and the external control signal, produce a current that sets the resistance of said first active resistor implemented by said first transistor and a current that sets the resistance of said second active resistor implemented by said second transistor respectively.

5. The AC signal generator of claim 4, wherein said control circuit of said linear amplifier:
   is configured to combine the feedback signal from said differential amplifier with the external control signal to produce a feedback adjusted external control signal, the feedback adjusted external control signal having both positive and negative components; and
   said control circuit includes a rectifier and splitter that receives the feedback adjusted external control signal and that provides a negative component of the feedback adjusted external control signal as a control signal to said first voltage controlled current source and a positive component of the feedback adjusted external control signal as a control signal to said second voltage controlled current source.

6. The AC signal generator of claim 1, further comprising:
   a power supply for supplying a variable DC voltage to the center tap of said transformer primary winding;
   a headroom monitor that monitors the voltage across said first and second transistors and that produces a signal representative of the voltage across said first and second transistors; and
   a power supply controller that receives from said headroom monitor the signal representative of the voltage across said first transistor and the voltage across said second transistor, that is connected to said power supply for regulating the DC voltage supplied by said power supply, and that is configured to, based on the voltage across said first and second transistors indicated by said headroom monitor, set the level of the DC voltage said power supply supplies to the transformer primary winding.

7. The AC signal generator of claim 6, wherein said headroom monitor is configured to receive as inputs, if said first and second transistors are FETs, the voltages present at the drains and sources of the FETs and, if said first and second transistors are bipolar transistors, the voltages present at the collectors and emitters of the bipolar transistors.

8. The AC signal generator of claim 6, wherein said DC power supply includes a constant DC voltage supply and a boost converter to which DC voltage from said constant DC voltage supply is applied and that is configured to, in response to a control signal from said power supply controller, apply a varying DC voltage to the center tap of said transformer primary winding.

9. The AC signal generator of claim 1, wherein said first and second transistors of said linear amplifier that function as said first and second active resistors respectively are MOSFETs.

10. The AC signal generator of claim 1, wherein said linear amplifier is configured to, independent of the feedback signal and the external control signal, apply a signal to each of said first and second transistors so each of said first and second transistors is continually in a saturation mode.

11. An ultrasonic surgical tool system comprising:
an AC signal generator including:
a transformer with: a primary winding with opposed ends and a center tap to which a DC voltage is applied; and a secondary winding across which an AC drive signal is induced for application to a power generating unit of a surgical tool; and
a linear amplifier, said linear amplifier including:
first and second transistors that function as first and second active resistors respectively that are each connected to a separate end of the opposed ends of said primary winding of said transformer and ground, wherein said linear transformer is configured to set the resistances of said first and second active resistors to set the voltage at each opposed end of the primary winding between a ground state voltage and an open state voltage that causes an AC voltage to develop across the primary winding that causes the AC drive signal to develop across said secondary winding;
a differential amplifier to which the voltages present at the opposed ends of the transformer primary winding are applied and that said differential amplifier produces as a feedback signal a signal based on the differences between the voltages present at the opposed ends of the transformer primary winding; and
a control circuit that receives the feedback signal and an external control signal and that, based on the feedback signal and the external control signal, sets the resistances of said first and second active resistors for generating a substantially linear response responsive to the external control signal;
a power supply for supplying a variable DC voltage to the center tap of said transformer primary winding;
a headroom monitor that monitors the voltage across said first and second transistors and that produces a signal representative of the voltage across said first and second transistors;
a power supply controller that receives from said headroom monitor the signal representative of the voltage across said first transistor and the voltage across said second transistor, that is connected to said power supply for regulating the DC voltage supplied by said power supply, and that is configured to, based on the voltage across said first and second transistors, set the level of the DC voltage said power supply supplies to the transformer primary winding; and
a handpiece including at least one driver that is connected to said secondary winding of said transformer and is actuated upon the application of the AC drive signal to said driver, and a tip that is connected to said at least one driver and vibrates upon actuation of said at least one driver.

12. An AC signal generator for an ultrasonic handpiece including a driver and a tip coupled to the driver that vibrates upon actuation of the driver, the AC signal generator comprising:
a transformer including a primary winding with opposed ends and a center tap to which a DC voltage is applied; and a secondary winding across which an AC drive signal is induced for actuating the driver of the handpiece;
a first transistor connected between a first end of said primary winding and ground and a second transistor connected between a second end of said primary winding and ground, wherein said first and second transistors operate as first and second active resistors respectively between the first and second ends of the primary winding respectively and ground to set the voltage across each of the first and second ends of said primary winding to cause an AC voltage to develop across the primary winding that causes the AC drive signal to develop across said secondary winding;
a variable DC power supply assembly regulating the level of the DC voltage applied to the center tap of the transformer primary winding; and
a headroom monitor connected to ends of said first transistor and said second transistor that are connected to the first and second ends of said primary winding of said transformer respectively, wherein said headroom monitor is configured to, based on the voltages present at the ends of the first and second transistors, generate a headroom signal representative of the headroom voltages at the first and second transistors,
wherein said variable DC power supply is configured to, based on the headroom signal received from said headroom monitor, set the level of the DC voltage applied to the center tap of the transformer primary winding to cause saturation voltages to be applied to said first transistor and said second transistor for causing, responsive to receipt of an external control signal, a proportional change in the AC voltage developed across said primary winding that causes desired vibrations of the handpiece upon actuation of the driver by the AC drive signal developed across the secondary winding according to the external control signal.

13. The AC signal generator of claim 12, wherein said headroom monitor is further configured to receive as inputs the voltages present at the opposed ends of said first and second transistors and to generate the signal representative of headroom voltage based on a difference between the voltages present at the opposed ends of said first and second transistors.

14. The AC signal generator of claim 12, further comprising:
a controller for regulating the currents applied to said first and second transistors to regulate the level of the voltages that develop across said primary winding of said transformer, said controller being configured to:
determine voltages to be developed across the transformer primary winding;
prior to the controller causing the determined voltages to develop across the transformer primary winding, calculate an anticipated headroom voltage based on the determined voltages and the level of the DC voltage currently applied to the center tap; and
adjust the level of the DC voltage applied to the center tap of the transformer primary winding based on the anticipated headroom voltage.

15. The AC signal generator of claim 14, wherein said controller is further configured to, responsive to the determined voltages to be developed across said primary winding of said transformer being a decrease in the voltages across said primary winding of said transformer, lower the level of the DC voltage applied to the center tap of the transformer primary winding at a rate that is slower than the rate at which the voltages across said primary winding is to be decreased.

16. The AC signal generator of claim 12, wherein:
said first and second transistors are FETs; and
said headroom monitor is configured to generate a signal representative of headroom voltage based on the difference between the lower of the two drain voltages of said first and second transistors and the higher of the two peak voltages at the sources of said first and second transistors.

17. The AC signal generator of claim 12, wherein said headroom monitor is constructed so that:
the voltages present at each junction between said first transistor and said second transistor and said primary winding of said transformer is applied to a reverse biased diode;
the anodes of said diodes are connected together; and
a constant voltage is applied to the junction of the anodes so that the voltage present at the junction of the anodes of said diodes is the lower of the two voltages present between the transistors and the transformer primary winding and this voltage is used as the voltage present at first ends of the transistors.

18. The AC signal generator of claim 12, wherein said headroom monitor is constructed so that the voltages present at ends of said first and second transistors distal to the transformer primary winding are applied to separate forward biased diodes, the cathodes of said diodes are connected at a junction and the voltage present at the junction of the diodes is used as the voltage present at first ends of the first and second transistors.

19. An AC signal generator for an ultrasonic handpiece including a driver and a tip coupled to the driver that vibrates upon actuation of the driver, the AC signal generator comprising:
a transformer including a primary winding with opposed ends and a center tap to which a DC voltage is applied; and a secondary winding across which an AC drive signal is induced for actuating the driver of the handpiece;
a first transistor tied to a first end of the opposed ends of said primary winding of said transformer and a second transistor tied to a second end of the opposed ends of said primary winding, wherein the first and second transistors are selectively turned on/off to cause an AC voltage to develop across said primary winding;
a control assembly that varies the signal applied to the bases or gates of the first and second transistors to cause the first and second transistors to function as first and second active resistors respectively; and
an inductor connected between at one end a junction of said first transistor and the first end of said primary winding of said transformer and at an opposed end to a junction of said second transistor and the second end of said primary winding for reducing an extent to which voltage across and current through the first and second transistors are out of phase, wherein said inductor has an inductance such that a circuit including said inductor in parallel with said at least one driver of said handpiece has a resonant frequency within 50% of the resonant frequency of said handpiece.

20. An AC signal generator for an ultrasonic handpiece including a driver and a tip coupled to the driver that vibrates upon actuation of the driver, the AC signal generator comprising:
a transformer including a primary winding with opposed ends and a center tap to which a DC voltage is applied; and a secondary winding across which an AC drive signal is induced for actuating the driver of the handpiece;
a first transistor connected between a first end of the opposed ends of said primary winding of said transformer and ground and a second transistor tied to a second end of the opposed ends of said primary winding and ground, wherein each of said first transistor and said second transistor is selectively turned on/off to cause an AC voltage to develop across the primary winding;
a variable DC power supply assembly regulating the level of the DC voltage applied to the center tap of the transformer primary winding;
a headroom monitor connected to a junction of said first transistor and the first end of said primary winding of said transformer and to a junction of said second transistor and the second end of said primary winding, wherein said headroom monitor is configured to, based on the voltages present at the first and second ends of said primary winding, generate a signal representative of the headroom voltages at the transistors; and
a control circuit that applies variable currents to the first and second transistors so that the first and second transistors function as first and second active resistors respectively, wherein said control circuit receives from said headroom monitor the headroom signal and is further configured to, based on the headroom signal, regulate the currents applied to said first and second transistors to selectively limit the voltage that appears across the transformer primary winding for causing, responsive to receipt of an external control signal, a proportional change in the AC voltage developed across the primary winding that causes desired vibrations of the tip of the handpiece upon actuation of the driver by the AC drive signal developed across the secondary winding according to the external control signal.

21. The AC signal generator of claim 20, wherein said headroom monitor is further configured to receive as inputs the voltages present at opposed ends of said first and second transistors and to generate the signal representative of headroom voltage based on a difference between the voltages present at first ends of the first and second transistors and the voltages present at second ends of the first and second transistors, the second ends opposite the first ends.

22. The AC signal generator of claim 20, wherein:
said first and second transistors are FETs; and
said headroom monitor is configured to generate a signal representative of headroom voltage based on the difference between the lower of the two drain voltages of the first and second transistors and the higher of the two peak voltages at the sources of the first and second transistors.

23. The AC signal generator of claim 20, wherein: said headroom monitor is constructed so that the voltages present at each junction between said first and second transistors and said primary winding of said transformer is applied to a reverse biased diode; the anodes of said diodes are connected together; and a constant voltage is applied to the junction of the anodes so that the voltage present at the junction of the anodes of said diodes is the lower of the two voltages present between the first and second transistors and the transformer primary winding and this voltage is used as the voltage present at first ends of said first and second transistors.

24. The AC signal generator of claim 20, wherein said headroom monitor is constructed so that the voltages present at the ends of said first and second transistors distal to said transformer primary winding are applied to separate forward biased diodes, the cathodes of said diodes are connected at a junction and the voltage present at the junction of said diodes is used as the voltage present at first ends of said firsts and second transistors.

* * * * *